(12) United States Patent
Burch et al.

(10) Patent No.: US 8,486,975 B2
(45) Date of Patent: Jul. 16, 2013

(54) NON-NUCLEOSIDE REVERSE TRANSCRIPTASE INHIBITORS

(75) Inventors: Jason Burch, Redwood City, CA (US); Bernard Cote, Notre-Dame-de-I'lle-Perrot (CA)

(73) Assignee: Merck Canada Inc., Kirkland, Quebec (CA)

( * ) Notice: Subject to any disclaimer, the term of this patent is extended or adjusted under 35 U.S.C. 154(b) by 193 days.

(21) Appl. No.: 13/073,631

(22) Filed: Mar. 28, 2011

(65) Prior Publication Data

US 2011/0245296 A1 Oct. 6, 2011

Related U.S. Application Data

(60) Provisional application No. 61/318,824, filed on Mar. 30, 2010, provisional application No. 61/321,573, filed on Apr. 7, 2010.

(51) Int. Cl.
*A61K 31/4439* (2006.01)
*C07D 401/06* (2006.01)

(52) U.S. Cl.
USPC ........................................ 514/340; 546/272.4

(58) Field of Classification Search
USPC ........................................ 546/272.4; 514/340
See application file for complete search history.

(56) References Cited

U.S. PATENT DOCUMENTS

| 2004/0192704 A1 | 9/2004 | Dunn et al. |
| 2010/0256181 A1 | 10/2010 | Tucker et al. |

FOREIGN PATENT DOCUMENTS

| CA | 2515151 A1 | 2/2004 |
| CA | 2518437 A1 | 3/2004 |
| CA | 2705834 A1 | 11/2008 |

OTHER PUBLICATIONS

Dorwald, Side Reactions in Organic Synthesis, 2005, Wiley: VCH Weinheim Preface, pp. 1-15 & Chapter 8, pp. 279-308.*
Sweeney, Zachary K. et al., "Discovery of triazolinone non-nucleoside inhibitors of HIV reverse transcriptase", Bioorganic & Medicinal Chemistry Letters, 2008, pp. 4348-4351, vol. 18.
Written Opinion of the International Searching Authority and International Search Report from counterpart PCT Application No. PCT/CA2011/000320 filed Mar. 28, 2011.

* cited by examiner

*Primary Examiner* — Patricia L Morris
(74) *Attorney, Agent, or Firm* — Sheldon Heber; Raynard Yuro

(57) ABSTRACT

Heteroaromatic compounds of Formula I:

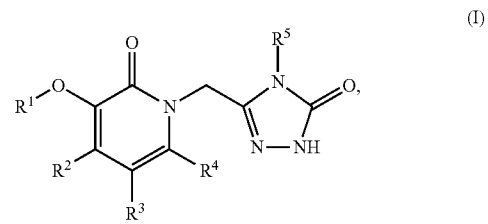

are HIV reverse transcriptase inhibitors, wherein $R^1$, $R^2$, $R^3$, $R^4$ and $R^5$ are defined herein. The compounds of Formula I and their pharmaceutically acceptable salts are useful in the inhibition of HIV reverse transcriptase, the prophylaxis and treatment of infection by HIV and in the prophylaxis, delay in the onset or progression, and treatment of AIDS. The compounds and their salts can be employed as ingredients in pharmaceutical compositions, optionally in combination with other antivirals, immunomodulators, antibiotics or vaccines.

6 Claims, No Drawings

NON-NUCLEOSIDE REVERSE TRANSCRIPTASE INHIBITORS

CROSS-REFERENCE TO RELATED APPLICATIONS

The present application claims the benefit of U.S. provisional application Nos. 61/318,824 filed Mar. 30, 2010 and 61/321,573 filed Apr. 7, 2010, both of which are incorporated by reference.

FIELD OF THE INVENTION

The present invention is directed to certain 3-(optionally substituted aromatic and aliphatic hydrocarbyloxy)-1-[(5-oxo-4,5-dihydro-1H-1,2,4-triazol-3-yl)methyl])-pyridin-2(1H)-one compounds and their use for the inhibition of HIV reverse transcriptase, the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'- dideoxycytidine (ddC), d4T, 3TC, nevirapine, delavirdine, efavirenz, abacavir, emtricitabine, and tenofovir.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a particular need for new RT inhibitors that are effective against mutant HIV strains.

The following references are of interest as background:

Clemo et al., *J. Chem. Soc.* 1954, pp. 2693-2702 discloses certain derivatives of the 4-oxo-3-(2-pyridyl)pyridocoline system and in particular discloses 6-methyl-6'-phenoxy-2,2'-methylenedipyridine.

Sweeney et al. *Bioorganic & Medicinal Chem. Letters* 2008, vol. 18, pp. 4348-4351 discloses a series of triazolinones that were found to be non-nucleoside inhibitors of HIV reverse transcriptase.

WO 2001/034578 discloses certain substituted azoles (including, for example, certain imidazoles and benzimidazoles) having anti-*Helicobacter pylori* activity. In particular, WO '578 discloses 1-[(3-methyl-4-phenoxy-2-pyridinyl)methyl]-1H-benzimidazole (see Compound 91 on page 40).

WO 2004/085406 and corresponding U.S. Pat. No. 7,189,718 disclose certain benzyl pyridazinones as reverse transcriptase inhibitors.

WO 2005/102989 and corresponding U.S. Pat. No. 7,166,738 disclose certain N-phenyl 2-phenylacetamides to be non-nucleoside reverse transcriptase inhibitors.

WO 2006/067587 discloses certain biaryl ether derivatives to be modulators of the reverse transcriptase enzyme.

WO 2007/045572 and WO 2007/045573 disclose certain 2-(2-phenoxyphenyl) N-phenyl acetamides as non-nucleoside reverse transcriptase inhibitors.

WO 2008/076225 discloses certain indazoles, benzotriazoles and related bicyclic compounds as HIV reverse transcriptase inhibitors.

WO 2009/067166 discloses certain aryloxy-, cycloalkyloxy-, and heterocyclyloxy-pyridines and related compounds. The compounds are HIV reverse transcriptase inhibitors suitable, for example, for the treatment of infection by HIV. Among the compounds disclosed are certain 3-(3,5-disubstituted phenoxy)-1-(1H-pyrazolo[3,4-b]pyridin-3-ylmethyl)-4-(substituted)pyridin-2(1H)-ones.

US 2004/0192704 discloses certain 3-(phenoxy)benzyl substituted 5-membered triazolones, oxadiazolones, and thiadiazolones. The compounds are disclosed to be non-nucleoside reverse transcriptase inhibitors useful for the treatment or prophylaxis of HIV mediated diseases.

US 2007/0021442 and WO 2007/015812 disclose certain substituted aromatic compounds. The compounds are HIV reverse transcriptase inhibitors suitable, for example, for the treatment of infection by HIV.

SUMMARY OF THE INVENTION

The present invention is directed to certain 3-(optionally substituted phenoxy)-1-[(5-oxo-4,5-dihydro-1H-1,2,4-triazol-3-yl)methyl])-pyridin-2(1H)-one compounds and their use in the inhibition of HIV reverse transcriptase, the prophylaxis of infection by HIV, the treatment of infection by HIV, and the prophylaxis, treatment, and delay in the onset or progression of AIDS and/or ARC. More particularly, the present invention includes compounds of Formula I and pharmaceutically acceptable salts thereof:

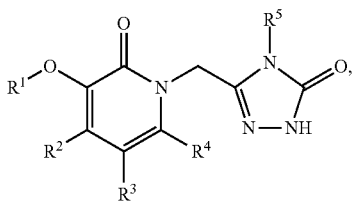

(I)

wherein:
$R^1$ is $C_{1-10}$ alkyl, CycA, or AryA;
CycA is $C_{3-8}$ cycloalkyl, wherein the cycloalkyl is optionally substituted with from 1 to 4 substituents, each of which is independently halogen, $C_{1-6}$ alkyl, OH, O—$C_{1-6}$ alkyl, $C_{1-6}$ haloalkyl, or O—$C_{1-6}$ haloalkyl;
AryA is aryl which is optionally substituted with a total of from 1 to 6 substituents, wherein:
(i) from zero to 6 substituents are each independently:
(1) $C_{1-6}$ alkyl,
(2) $C_{1-6}$ haloalkyl,
(3) $C_{1-6}$ alkyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(4) $C_{2-6}$ alkenyl,
(5) $C_{2-6}$ alkenyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(6) $C_{2-6}$ alkynyl,
(7) $C_{2-6}$ alkynyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(8) O—$C_{1-6}$ alkyl,
(9) O—$C_{1-6}$ haloalkyl,
(10) OH,
(11) halogen,
(12) CN,
(13) $NO_2$,
(14) $N(R^A)R^B$,
(15) $C(O)N(R^A)R^B$,
(16) $C(O)R^A$,
(17) $C(O)$—$C_{1-6}$ haloalkyl,
(18) $C(O)OR^A$,
(19) $OC(O)N(R^A)R^B$,
(20) $SR^A$,
(21) $S(O)R^A$,
(22) $S(O)_2R^A$,
(23) $S(O)_2N(R^A)R^B$,
(24) $N(R^A)S(O)_2R^B$,
(25) $N(R^A)S(O)_2N(R^A)R^B$,
(26) $N(R^A)C(O)R^B$,
(27) $N(R^A)C(O)N(R^A)R^B$,
(28) $N(R^A)C(O)$—$C(O)N(R^A)R^B$, or
(29) $N(R^A)CO_2R^B$, and
(ii) from zero to 2 substituents are each independently:
(1) CycQ,
(2) AryQ,
(3) HetQ,
(4) HetR,
(5) J-CycQ,
(6) J-AryQ,
(7) J-HetQ,
(8) J-HetR,
(9) $C_{1-6}$ alkyl substituted with CycQ, AryQ, HetQ, HetR, J-CycQ, J-AryQ, J-HetQ, or J-HetR,
(10) $C_{2-6}$ alkenyl substituted with CycQ, AryQ, HetQ, HetR, J-CycQ, J-AryQ, J-HetQ, or J-HetR, or
(11) $C_{2-6}$ alkynyl substituted with CycQ, AryQ, HetQ, HetR, J-CycQ, J-AryQ, J-HetQ, or J-HetR;
each CycQ is independently $C_{3-8}$ cycloalkyl or $C_{5-8}$ cycloalkenyl, wherein the cycloalkyl or cycloalkenyl is optionally substituted with from 1 to 4 substituents, each of which is independently halogen, $C_{1-6}$ alkyl, OH, O—$C_{1-6}$ alkyl, $C_{1-6}$ haloalkyl, or O—$C_{1-6}$ haloalkyl;
each AryQ is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;
each HetQ is independently a heteroaryl which is optionally substituted with from 1 to 4 substituents each of which is independently halogen, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SO_2R^A$, $N(R^A)C(O)N(R^A)R^B$, or $N(R^A)CO_2R^B$;
each HetR is independently a 4- to 7-membered, saturated or unsaturated, non-aromatic heterocyclic ring (e.g., a mono-unsaturated heterocyclic ring) containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)N(R^A)R^B$, $C(O)R^A$, $CO_2R^A$, or $SO_2R^A$;
each J is independently:
(i) O,
(ii) S,
(iii) S(O),
(iv) $S(O)_2$,
(v) O—$C_{1-6}$ alkylene,
(vi) S-$C_{1-6}$ alkylene,
(vii) S(O)—$C_{1-6}$ alkylene,
(viii) $S(O)_2$—$C_{1-6}$ alkylene,
(ix) $N(R^A)$, or
(x) $N(R^A)$—$C_{1-6}$alkylene;
$R^2$ and $R^3$ are each independently:
(1) H,
(2) $C_{1-6}$ alkyl,
(3) $C_{1-6}$ haloalkyl,
(4) $C_{1-6}$ alkyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)$ C(O)$R^B$, N($R^A$)CO$_2$$R^B$, N($R^A$)S(O)$_2$$R^B$, N($R^A$)S(O)$_2$N($R^A$)$R^B$,) OC(O)N($R^A$)$R^B$, N($R^A$)C(O)N($R^A$)$R^B$, or N($R^A$)C(O)C(O)N($R^A$)$R^B$, (5) O—$C_{1-6}$ alkyl in which the alkyl is optionally substituted with OH, O—$C_{1-6}$ alkyl, O—$C_{1-6}$ haloalkyl, CN, N($R^A$)$R^B$, C(O)N($R^A$)$R^B$, C(O)$R^A$, CO$_2$$R^A$, S$R^A$, S(O)$R^A$, S(O)$_2$$R^A$, or S(O)$_2$N($R^A$)$R^B$,
(6) O—$C_{1-6}$ haloalkyl,
(7) halogen,
(8) CN,
(9) NO$_2$,
(10) N($R^A$)$R^B$,
(11) C(O)N($R^A$)$R^B$,
(12) C(O)$R^A$,
(13) C(O)—$C_{1-6}$ haloalkyl,
(14) C(O)O$R^A$,
(15) OC(O)$R^A$,
(16) OC(O)N($R^A$)$R^B$,
(17) S$R^A$,
(18) S(O)$R^A$,
(19) S(O)$_2$$R^A$,
(20) S(O)$_2$N($R^A$)$R^B$,
(21) N($R^A$)S(O)$_2$$R^B$,
(22) N($R^A$)S(O)$_2$N($R^A$)$R^B$,
(23) N($R^A$)C(O)$R^B$,
(24) N($R^A$)C(O)N($R^A$)$R^B$,
(25) N($R^A$)C(O)—C(O)N($R^A$)$R^B$,
(26) N($R^A$)CO$_2$$R^B$,
(27) N($R^C$)$R^D$,
(28) C(O)N($R^C$)$R^D$,
(29) OC(O)N($R^C$)$R^D$,
(30) S(O)$_2$N($R^C$)$R^D$,
(31) N($R^A$)S(O)$_2$N($R^C$)$R^D$,
(32) N($R^A$)C(O)N($R^C$)$R^D$,
(33) N($R^A$)C(O)—C(O)N($R^C$)$R^D$,
(34) $C_{3-8}$ cycloalkyl,
(35) O—$C_{3-8}$ cycloalkyl,
(36) AryX, or
(37) HetX;
    wherein AryX independently has the same definition as AryQ, and HetX independently has the same definition as HetQ;
$R^4$ is H, $C_{1-6}$ alkyl, AryZ, HetZ, halogen, CN, or $C_{1-6}$ fluoroalkyl;
AryZ independently has the same definition as AryQ;
HetZ independently has the same definition as HetQ;
$R^5$ is H or $C_{1-6}$ alkyl;
each aryl is independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic;
each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered heterobicyclic, fused ring system containing from 1 to 6 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or S(O)$_2$;
each $R^A$ is independently H or $C_{1-6}$ alkyl;
each $R^B$ is independently H or $C_{1-6}$ alkyl; and
each pair of $R^C$ and $R^D$ together with the nitrogen to which they are both attached form a 4- to 7-membered saturated or unsaturated, non-aromatic ring (e.g., a mono-unsaturated ring) which optionally contains a heteroatom in addition to the N to which $R^C$ and $R^D$ are attached, wherein the additional heteroatom is selected from N, O, and S; wherein the ring is optionally substituted with 1 or 2 substituents each of which is independently $C_{1-6}$ alkyl, C(O)$R^A$, C(O)O$R^A$, C(O)N($R^A$)$R^B$, or S(O)$_2$$R^A$; and wherein the optional S in the ring is optionally in the form of S(O) or S(O)$_2$.

The present invention also includes pharmaceutical compositions containing a compound of Formula I or a pharmaceutically acceptable salt thereof. The present invention further includes methods involving compounds of Formula I for the treatment of AIDS, the delay in the onset or progression of AIDS, the prophylaxis of AIDS, the prophylaxis of infection by HIV, and the treatment of infection by HIV.

Other embodiments, aspects, classes, sub-classes and features of the present invention are either further described in or will be apparent from the ensuing description, examples and appended claims.

DETAILED DESCRIPTION OF THE INVENTION

The compounds of Formula I above, and pharmaceutically acceptable salts thereof, are HIV reverse transcriptase inhibitors. The compounds are useful for inhibiting HIV reverse transcriptase and for inhibiting HIV replication in vitro and in vivo. More particularly, the compounds of Formula I inhibit the polymerase function of HIV-1 reverse transcriptase. Based upon the testing of representative compounds of the invention in the assay set forth in Example 9 below, it is known that compounds of Formula I inhibit the RNA-dependent DNA polymerase activity of HIV-1 reverse transcriptase. Representative compounds of the present invention (see, e.g., the compounds of Examples 1 to 8) also exhibit activity against drug resistant forms of HIV (e.g., mutant strains of HIV-1 in which reverse transcriptase has a mutation at lysine 103→asparagine (K103N) and/or tyrosine 181→cysteine (Y181C)), and thus can exhibit decreased cross-resistance against currently approved antiviral therapies.

A first embodiment of the present invention (alternatively referred to herein as "Embodiment E1") is a compound of Formula I (alternatively and more simply referred to as "Compound I"), or a pharmaceutically acceptable salt thereof, wherein each CycQ is independently $C_{3-8}$ cycloalkyl, wherein the cycloalkyl is optionally substituted with from 1 to 4 substituents, each of which is independently halogen, $C_{1-4}$ alkyl, OH, O—$C_{1-4}$ alkyl, $C_{1-4}$ haloalkyl, or O—$C_{1-4}$ haloalkyl; and all other variables in Formula I are as originally defined (i.e., as defined in the Summary of the Invention).

A second embodiment of the present invention (Embodiment E2) is a compound of Formula I, or a pharmaceutically acceptable salt thereof, wherein each CycQ is independently $C_{3-7}$ cycloalkyl, wherein the cycloalkyl is optionally substituted with from 1 to 3 substituents, each of which is independently halogen, $C_{1-4}$ alkyl, OH, O—$C_{1-4}$ alkyl, $C_{1-4}$ haloalkyl, or O—$C_{1-4}$ haloalkyl; and all other variables are as originally defined.

A third embodiment of the present invention (Embodiment E3) is a compound of Formula I, or a pharmaceutically acceptable salt thereof, wherein each CycQ is independently $C_{3-7}$ cycloalkyl, wherein the cycloalkyl is optionally substituted with from 1 to 3 substituents, each of which is independently Cl, Br, F, CH$_3$, OH, OCH$_3$, CF$_3$, or OCF$_3$; and all other variables are as originally defined.

A fourth embodiment of the present invention (Embodiment E4) is a compound of Formula I, or a pharmaceutically acceptable salt thereof, wherein AryQ is phenyl or naphthyl, wherein the phenyl or naphthyl is optionally substituted with from 1 to 3 substituents each of which is independently halogen, CN, NO$_2$, C$_{1-4}$ alkyl, C$_{1-4}$ haloalkyl, OH, O—C$_{1-4}$ alkyl, O—C$_{1-4}$ haloalkyl, N(R$^A$)R$^B$, C(O)N(R$^A$)R$^B$, C(O)R$^A$, CO$_2$R$^A$, SR$^A$, S(O)R$^A$, SO$_2$R$^A$, SO$_2$N(R$^A$)R$^B$, or SO$_2$N(R$^A$)C(O)R$^B$; and all other variables are as originally defined or as defined in any one of Embodiments E1 to E3. In an aspect of this embodiment, any R$^A$ or R$^B$ which is part of AryQ is H or C$_{1-4}$ alkyl. As noted below, when any variable that occurs more than once in Formula I, its definition at each occurrence is independent of its definition at the other occurrences; thus, it is understood that the definitions of R$^A$ and R$^B$ for AryQ in this aspect are independent of and do not necessarily apply to the definitions of R$^A$ and R$^B$ that occur elsewhere in Formula I.

A fifth embodiment of the present invention (Embodiment E5) is a compound of Formula I, or a pharmaceutically acceptable salt thereof, wherein AryQ is phenyl, which is optionally substituted with from 1 to 3 substituents each of which is independently Cl, Br, F, CN, CH$_3$, CF$_3$, OH, OCH$_3$, OCF$_3$, NH$_2$, N(H)CH$_3$, N(CH$_3$)$_2$, C(O)NH$_2$, C(O)N(H)CH$_3$, C(O)N(CH$_3$)$_2$, C(O)CH$_3$, C(O)CF$_3$, CO$_2$CH$_3$, S(O)$_2$CH$_3$, or SO$_2$NH$_2$; and all other variables are as originally defined or as defined in any one of Embodiments E1 to E3.

A sixth embodiment of the present invention (Embodiment E6) is a compound of Formula I, or a pharmaceutically acceptable salt thereof, wherein AryQ is phenyl, which is optionally substituted with from 1 or 2 substituents each of which is independently Cl, Br, F, CN, CH$_3$, CF$_3$, OH, OCH$_3$, or OCF$_3$; and all other variables are as originally defined or as defined in any one of Embodiments E1 to E3.

A seventh embodiment of the present invention (Embodiment E7) is a compound of Formula I, or a pharmaceutically acceptable salt thereof, wherein HetQ is a 5- or 6-membered heteroaromatic ring containing a total of from 1 to 4 heteroatoms each of which is independently selected from N, O and S, wherein the heteroaromatic ring is optionally substituted with from 1 to 3 substituents each of which is independently:
(1) C$_{1-4}$ alkyl,
(2) C$_{1-4}$ fluoroalkyl,
(3) O—C$_{1-4}$ alkyl,
(4) O—C$_{1-4}$ fluoroalkyl,
(5) OH,
(6) C(O)R$^A$,
(7) CO$_2$R$^A$, or
(8) SO$_2$R$^A$;
and all other variables are as originally defined or as defined in any of one of Embodiments E1 to E6. In an aspect of Embodiment E7, the heteroaromatic ring contains a total of from 1 to 4 heteroatoms independently selected from 1 to 4 N atoms, zero or 1 O atom, and zero or 1 S atom. In another aspect of this embodiment, any R$^A$ or R$^B$ which is part of HetQ is H or C$_{1-4}$ alkyl. In still another aspect of this embodiment, the heteroaromatic ring contains a total of from 1 to 4 heteroatoms independently selected from 1 to 4 N atoms, zero or 1 O atom, and zero or 1 S atom; and any R$^A$ or R$^B$ which is part of HetQ is H or C$_{1-4}$ alkyl.

An eighth embodiment of the present invention (Embodiment E8) is a compound of Formula I, or a pharmaceutically acceptable salt thereof, wherein HetQ is a heteroaromatic ring selected from the group consisting of pyrrolyl, pyrazolyl, imidazolyl, pyridinyl, pyrimidinyl, pyrazinyl, oxazolyl, isoxazolyl, thiazolyl, isothiazolyl, oxadiazolyl, and thiadiazolyl, wherein the heteroaromatic ring is optionally substituted with from 1 to 2 substituents each of which is independently a C$_{1-4}$ alkyl; and all other variables are as originally defined or as defined in any one of Embodiments E1 to E6.

A ninth embodiment of the present invention (Embodiment E9) is a compound of Formula I, or a pharmaceutically acceptable salt thereof, wherein HetR is a 4- to 7-membered, saturated heterocyclic ring containing an N atom and optionally containing an additional heteroatom selected from N, O and S, wherein (i) the heterocyclic ring is attached to the rest of the compound via an N atom, (ii) the optional S atom is optionally oxidized to S(O) or S(O)$_2$, and (iii) the heterocyclic ring is optionally substituted with from 1 to 3 substituents, each of which is independently:
(1) C$_{1-4}$ alkyl,
(2) C$_{1-4}$ fluoroalkyl,
(3) O—C$_{1-4}$ alkyl,
(4) O—C$_{1-4}$ fluoroalkyl,
(5) oxo,
(6) C(O)R$^A$,
(7) CO$_2$R$^A$, or
(8) SO$_2$R$^A$;
and all other variables are as originally defined or a defined in any one Embodiments E1 to E8.

A tenth embodiment of the present invention (Embodiment E10) is a compound of Formula I, or a pharmaceutically acceptable salt thereof, wherein HetR is a saturated heterocyclic ring selected from the group consisting of:

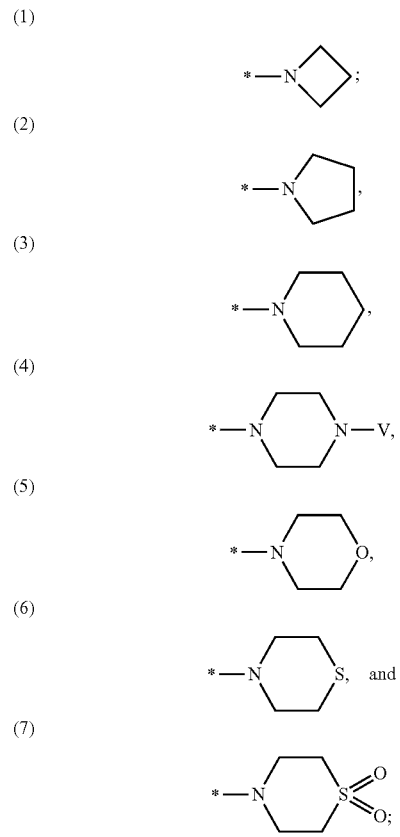

V is independently H, C$_{1-3}$ alkyl, C(O)—C$_{1-3}$ alkyl, C(O)—O—C$_{1-3}$ alkyl, or S(O)$_2$—C$_{1-3}$ alkyl; and all other variables are as originally defined or as defined in any one of Embodiments E1 to E8. In an aspect of this embodiment, V is independently H, CH$_3$, C(O)CH$_3$, C(O)OCH$_3$, or S(O)$_2$CH$_3$. In another aspect of this embodiment, V is CH$_3$, C(O)CH$_3$, C(O)OCH$_3$, or S(O)$_2$CH$_3$. In still another aspect of this embodiment, V is CH$_3$.

An eleventh embodiment of the present invention (Embodiment E11) is a compound of Formula I, or a pharmaceutically acceptable salt thereof, wherein each J is independently:
(i) O,
(ii) S,
(iii) S(O),
(iv) S(O)$_2$,
(v) O—(CH$_2$)$_{1-4}$,
(vi) S—(CH$_2$)$_{1-4}$,
(vii) S(O)—(CH$_2$)$_{1-4}$,
(viii) S(O)$_2$—(CH$_2$)$_{1-4}$,
(ix) N(R$^A$), or
(x) N(R$^A$)—(CH$_2$)$_{1-4}$;
and all other variables are as originally defined or as defined in any one of Embodiments E1 to E10.

A twelfth embodiment of the present invention (Embodiment E12) is a compound of Formula I, or a pharmaceutically acceptable salt thereof, wherein each J is independently:
(i) O,
(ii) S,
(iii) S(O),
(iv) S(O)$_2$,
(v) OCH$_2$,
(vi) SCH$_2$,
(vii) S(O)CH$_2$,
(viii) S(O)$_2$CH$_2$,
(ix) N(R$^A$), or
(x) N(R$^A$)CH$_2$;
and all other variables are as originally defined or as defined in any one of Embodiments E1 to E10.

A thirteenth embodiment of the present invention (Embodiment E13) is a compound of Formula I, or a pharmaceutically acceptable salt thereof, wherein AryA is phenyl or naphthyl, wherein the phenyl or naphthyl is optionally substituted with from 1 to 3 substituents each of which is independently:
(1) C$_{1-4}$ alkyl,
(2) C$_{1-4}$ haloalkyl,
(3) C$_{2-4}$ alkenyl,
(4) C$_{2-4}$ alkenyl substituted with CN,
(5) O—C$_{1-4}$ alkyl,
(6) O—C$_{1-4}$ haloalkyl,
(7) OH,
(8) halogen,
(9) CN,
(10) NO$_2$,
(11) N(R$^A$)R$^B$,
(12) C(O)N(R$^A$)R$^B$,
(13) C(O)R$^A$,
(14) CO$_2$R$^A$,
(15) SR$^A$,
(16) S(O)R$^A$,
(17) SO$_2$R$^A$,
(18) SO$_2$N(R$^A$)R$^B$,
(19) SO$_2$N(R$^A$)C(O)R$^B$, or
(20) CycQ, with the proviso that no more than 2 of the substituents are CycQ;
wherein each CycQ is C$_{3-7}$ cycloalkyl, wherein the cycloalkyl is optionally substituted with from 1 to 3 substituents, each of which is independently halogen, C$_{1-4}$ alkyl, OH, O—C$_{1-4}$ alkyl, C$_{1-4}$ haloalkyl, or O—C$_{1-4}$ haloalkyl; and all other variables in Formula I are as originally defined. In an aspect of this embodiment, any R$^A$ or R$^B$ which is part of AryA is H or C$_{1-4}$ alkyl.

A fourteenth embodiment of the present invention (Embodiment E14) is a compound of Formula I, or a pharmaceutically acceptable salt thereof, wherein AryA is phenyl, wherein the phenyl is optionally substituted with from 1 to 3 substituents each of which is independently:
(1) C$_{1-4}$ alkyl,
(2) C$_{1-4}$ haloalkyl,
(3) O—C$_{1-4}$ alkyl,
(4) halogen,
(5) CN,
(6) S—C$_{1-4}$ alkyl, or
(7) CycQ, with the proviso that no more than one substituent is CycQ, and wherein CycQ is C$_{3-7}$ cycloalkyl;
and all other variables are as originally defined. In an aspect of Embodiment E14, the C$_{1-4}$ haloalkyl substituent is C$_{1-4}$ fluoroalkyl; i.e., the 1 to 3 substituents are each independently (1) C$_{1-4}$ alkyl, (2) C$_{1-4}$ fluoroalkyl, (3) O—C$_{1-4}$ alkyl, (4) halogen, (5) CN, (6) S—C$_{1-4}$ alkyl, or (7) CycQ, with the proviso that no more than one substituent is CycQ, and wherein CycQ is C$_{3-7}$ cycloalkyl.

A fifteenth embodiment of the present invention (Embodiment E15) is a compound of Formula I, or a pharmaceutically acceptable salt thereof, wherein AryA is phenyl, wherein the phenyl is optionally substituted with from 1 to 2 substituents each of which is independently:
(1) CH$_3$,
(2) CF$_3$,
(3) CHF$_2$,
(4) CH$_2$CF$_3$,
(5) OCH$_3$,
(6) Cl,
(7) Br,
(8) F,
(9) CN,
(10) SCH$_3$, or
(11) cyclopropyl, with the proviso that no more than one substituent is cyclopropyl;
and all other variables are as originally defined.

A sixteenth embodiment of the present invention (Embodiment E16) is a compound of Formula I, or a pharmaceutically acceptable salt thereof, wherein AryA is phenyl which has two substituents, one of which is at the 3-position of the phenyl ring and the other is at the 5-position of the phenyl ring; and all other variables are as originally defined. In an aspect of Embodiment E16, the two substituents on the phenyl ring in AryA are independently selected from the list of substituents in Embodiment E13. In another aspect of this embodiment, the two substituents on the phenyl ring in AryA are independently selected from the list of substituents in Embodiment E14. In still another aspect of this embodiment, the two substituents on the phenyl ring in AryA are independently selected from the list of substituents in Embodiment E15.

A seventeenth embodiment of the present invention (Embodiment E17) is a compound of Formula I, or a pharmaceutically acceptable salt thereof, wherein AryA is

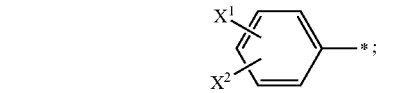

wherein X$^1$ and X$^2$ are each independently:
(1) H,
(2) C$_{1-4}$ alkyl,
(3) C$_{1-4}$ haloalkyl,
(4) C$_{2-4}$ alkenyl,
(5) C$_{2-4}$ alkenyl substituted with CN, (6) OH,
(7) O—$C_{1-4}$ alkyl,
(8) O—$C_{1-4}$ haloalkyl,
(9) halogen,
(10) CN,
(11) $NO_2$,
(12) $N(R^A)R^B$,
(13) $C(O)N(R^A)R^B$,
(14) $C(O)R^A$,
(15) $CO_2R^A$,
(16) $SR^A$,
(17) $S(O)R^A$,
(18) $SO_2R^A$,
(19) $SO_2N(R^A)R^B$,
(20) $SO_2N(R^A)C(O)R^B$, or
(21) CycQ; wherein:
each CycQ is $C_{3-7}$ cycloalkyl, wherein the cycloalkyl is optionally substituted with from 1 to 3 substituents, each of which is independently halogen, $C_{1-4}$ alkyl, OH, O—$C_{1-4}$ alkyl, $C_{1-4}$ haloalkyl, or O—$C_{1-4}$ haloalkyl;
and all other variables are as originally defined.

An eighteenth embodiment of the present invention (Embodiment E18) is a compound of Formula I, or a pharmaceutically acceptable salt thereof, wherein AryA is 3-chloro-5-cyanophenyl; and all other variables are as originally defined.

A nineteenth embodiment of the present invention (Embodiment E19) is a compound of Formula I, or a pharmaceutically acceptable salt thereof, wherein AryX independently has the same definition as AryQ as set forth in Embodiment E4; and all other variables are as originally defined or as defined in any one of the preceding embodiments.

A twentieth embodiment of the present invention (Embodiment E20) is a compound of Formula I, or a pharmaceutically acceptable salt thereof, wherein AryX independently has the same definition as AryQ as set forth in Embodiment E5; and all other variables are as originally defined or as defined in any one of the preceding embodiments.

A twenty-first embodiment of the present invention (Embodiment E21) is a compound of Formula I, or a pharmaceutically acceptable salt thereof, wherein AryX independently has the same definition as AryQ as set forth in Embodiment E6; and all other variables are as originally defined or as defined in any one of the preceding embodiments.

A twenty-second embodiment of the present invention (Embodiment E22) is a compound of Formula I, or a pharmaceutically acceptable salt thereof, wherein HetX independently has the same definition as HetQ as set forth in Embodiment E7; and all other variables are as originally defined or as defined in any one of the preceding embodiments.

A twenty-third embodiment of the present invention (Embodiment E23) is a compound of Formula I, or a pharmaceutically acceptable salt thereof, wherein HetX independently has the same definition as HetQ as set forth in Embodiment E8; and all other variables are as originally defined or as defined in any one of the preceding embodiments.

A twenty fourth embodiment of the present invention (Embodiment E24) is a compound of Formula I, or a pharmaceutically acceptable salt thereof, wherein AryZ independently has the same definition as AryQ as set forth in Embodiment E4; and all other variables are as originally defined or as defined in any one of the preceding embodiments.

A twenty-fifth embodiment of the present invention (Embodiment E25) is a compound of Formula I, or a pharmaceutically acceptable salt thereof, wherein AryZ independently has the same definition as AryQ as set forth in Embodiment E5; and all other variables are as originally defined or as defined in any one of the preceding embodiments.

A twenty-sixth embodiment of the present invention (Embodiment E26) is a compound of Formula I, or a pharmaceutically acceptable salt thereof, wherein AryZ independently has the same definition as AryQ as set forth in Embodiment E6; and all other variables are as originally defined or as defined in any one of the preceding embodiments.

A twenty-seventh embodiment of the present invention (Embodiment E27) is a compound of Formula I, or a pharmaceutically acceptable salt thereof, wherein HetZ independently has the same definition as HetQ as set forth in Embodiment E7; and all other variables are as originally defined or as defined in any one of the preceding embodiments.

A twenty-eighth embodiment of the present invention (Embodiment E28) is a compound of Formula I, or a pharmaceutically acceptable salt thereof, wherein HetZ independently has the same definition as HetQ as set forth in Embodiment E8; and all other variables are as originally defined or as defined in any one of the preceding embodiments.

A twenty-ninth embodiment of the present invention (Embodiment E29) is a compound of Formula I, or a pharmaceutically acceptable salt thereof, wherein $R^2$ and $R^3$ are each independently:
(1) H,
(2) $C_{1-4}$ alkyl,
(3) $C_{1-4}$ haloalkyl,
(4) $CH_2OH$,
(5) $CH_2O$—$C_{1-4}$ alkyl,
(6) $CH_2CN$,
(7) $CH_2N(R^A)R^B$,
(8) $CH_2C(O)N(R^A)R^B$,
(9) $CH_2C(O)R^A$,
(10) $CH_2CO_2R^A$,
(11) $CH_2S(O)_2R^A$,
(12) O—$C_{1-4}$ alkyl,
(13) O—$C_{1-4}$ haloalkyl,
(14) halogen,
(15) CN,
(16) $NO_2$,
(17) $N(R^A)R^B$,
(18) $C(O)N(R^A)R^B$,
(19) $C(O)R^A$,
(20) $C(O)$—$C_{1-4}$ haloalkyl,
(21) $C(O)OR^A$,
(22) $SR^A$,
(23) $S(O)_2R^A$, (24)

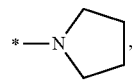

(25)

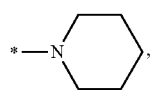

(26)

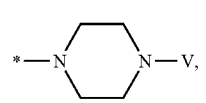

(27)

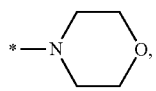

-continued

(28) 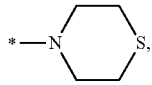

(29) 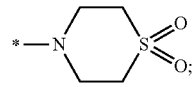

(30) 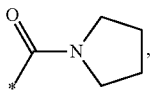

(31) 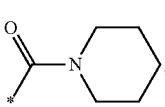

(32) 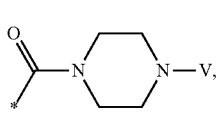

(33) 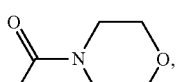

(34) 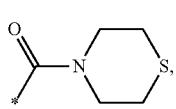

(35) 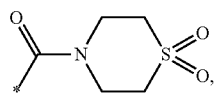

or
(36) $C_{3-7}$ cycloalkyl;
V is H, $CH_3$, $C(O)CH_3$, $C(O)OCH_3$, or $S(O)_2CH_3$; $R^4$ is H, $C_{1-4}$ alkyl, Cl, Br, F, CN, or $C_{1-4}$ fluoroalkyl; and all other variables are as originally defined or as defined in any one of Embodiments E1 to E18.

A thirtieth embodiment of the present invention (Embodiment E30) is a compound of Formula I, or a pharmaceutically acceptable salt thereof, wherein:
$R^2$ is:
 (1) $C_{1-4}$ alkyl,
 (2) $C_{1-4}$ haloalkyl,
 (3) O—$C_{1-4}$ alkyl,
 (4) O—$C_{1-4}$ halooalkyl,
 (5) halogen,
 (6) S—$C_{1-4}$ alkyl, or
 (7) $C_{3-7}$ cycloalkyl;
$R^3$ is:
 (1) H,
 (2) $C_{1-4}$ alkyl,
 (3) $C_{1-4}$ haloalkyl,
 (4) O—$C_{1-4}$ alkyl,
 (5) O—$C_{1-4}$ haloalkyl,
 (6) halogen,
 (7) S—$C_{1-4}$ alkyl, or
 (8) $C_{3-7}$ cycloalkyl;
$R^4$ is H; and all other variables are as originally defined or as defined in any one of Embodiments E1 to E18.

A thirty-first embodiment of the present invention (Embodiment E31) is a compound of Formula I, or a pharmaceutically acceptable salt thereof, wherein:
$R^2$ is:
 (1) $C_{1-4}$ alkyl,
 (2) $C_{1-4}$ fluoroalkyl,
 (3) O—$C_{1-4}$ alkyl,
 (4) O—$C_{1-4}$ fluoroalkyl,
 (5) Cl,
 (6) Br,
 (7) F,
 (8) S—$C_{1-4}$ alkyl, or
 (9) $C_{3-6}$ cycloalkyl; and
$R^3$ is:
 (1) $C_{1-4}$ alkyl,
 (2) $C_{1-4}$ fluoroalkyl,
 (3) O—$C_{1-4}$ alkyl,
 (4) O—$C_{1-4}$ fluoroalkyl,
 (5) Cl,
 (6) Br,
 (7) F,
 (8) S—$C_{1-4}$ alkyl, or
 (9) $C_{3-6}$ cycloalkyl;
$R^4$ is H; and all other variables are as originally defined or as defined in any one of Embodiments E1 to E18.

A thirty-second embodiment of the present invention (Embodiment E32) is a compound of Formula I, or a pharmaceutically acceptable salt thereof, wherein:
$R^2$ is:
 (1) $CH_3$,
 (2) $CF_3$,
 (3) $CF_2CH_3$,
 (4) $CH_2CF_3$,
 (5) $OCH_3$,
 (6) $OCF_3$,
 (7) Cl,
 (8) Br,
 (9) F,
 (10) $SCH_3$, or
 (11) cyclopropyl; and
$R^3$ is:
 (1) H,
 (2) $CH_3$,
 (3) $CF_3$,
 (4) $CF_2CH_3$,
 (5) $CH_2CF_3$,
 (6) $OCH_3$,
 (7) $OCF_3$,
 (8) Cl,
 (9) Br,
 (10) F,
 (11) $SCH_3$, or
 (12) cyclopropyl;
$R^4$ is H; and all other variables are as originally defined or as defined in any one of Embodiments E1 to E18.

A thirty-third embodiment of the present invention (Embodiment E33) is a compound of Formula I, or a pharmaceutically acceptable salt thereof, wherein:

$R^2$ is:
(1) $CH_3$,
(2) $CF_3$,
(3) $CF_2CH_3$,
(4) $CH_2CF_3$,
(5) $OCH_3$,
(6) $OCF_3$,
(7) Cl,
(8) Br,
(9) F,
(10) $SCH_3$, or
(11) cyclopropyl; and
$R^3$ is:
(1) H,
(2) Cl,
(3) Br, or
(4) F;
$R^4$ is H; and all other variables are as originally defined or as defined in any one of Embodiments E1 to E18. In an aspect of Embodiment E33, $R^3$ is H.

A thirty-fourth embodiment of the present invention (Embodiment E34) is a compound of Formula I, or a pharmaceutically acceptable salt thereof, wherein:
$R^2$ is $CF_3$, Cl, or Br; $R^3$ is H, Cl, Br, or F; $R^4$ is H; and all other variables are as originally defined or as defined in any one of Embodiments E1 to E18. In an aspect of Embodiment E34, $R^3$ is H.

A thirty-fifth embodiment of the present invention (Embodiment E35) is a compound of Formula I, or a pharmaceutically acceptable salt thereof, wherein $R^5$ is H or $C_{1-4}$ alkyl; and all other variables are as originally defined or as defined in any one of the preceding embodiments.

A thirty-sixth embodiment of the present invention (Embodiment E36) is a compound of Formula I, or a pharmaceutically acceptable salt thereof, wherein $R^5$ is H or $C_{1-3}$ alkyl; and all other variables are as originally defined or as defined in any one of the preceding embodiments.

A thirty-seventh embodiment of the present invention (Embodiment E37) is a compound of Formula I, or a pharmaceutically acceptable salt thereof, wherein $R^5$ is H, $CH_3$, or $CH_2CH_3$; and all other variables are as originally defined or as defined in any one of the preceding embodiments.

A thirty-eighth embodiment of the present invention (Embodiment E38) is a compound of Formula I, or a pharmaceutically acceptable salt thereof, wherein $R^A$ and $R^B$ are each independently H or $C_{1-4}$ alkyl; and all other variables are as originally defined or as defined in any of the preceding embodiments.

A thirty-ninth embodiment of the present invention (Embodiment E39) is a compound of Formula I, or a pharmaceutically acceptable salt thereof, wherein $R^A$ and $R^B$ are each independently H or $C_{1-3}$ alkyl; and all other variables are as originally defined or as defined in any of the preceding embodiments.

A fortieth embodiment of the present invention (Embodiment E40) is a compound of Formula I, or a pharmaceutically acceptable salt thereof, wherein $R^A$ and $R^B$ are each independently H or $CH_3$; and all other variables are as originally defined or as defined in any of the preceding embodiments.

A first class of compounds of the present invention (alternatively referred to herein as "Class C1") includes compounds of Formula II:

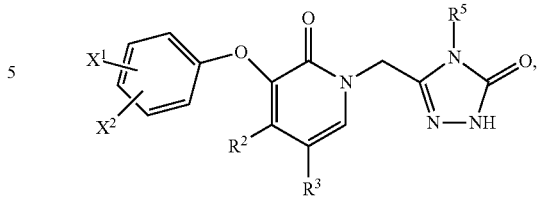

and pharmaceutically acceptable salts thereof, wherein:
$X^1$ and $X^2$ are each independently:
(1) H,
(2) $C_{1-4}$ alkyl,
(3) $C_{1-4}$ haloalkyl,
(4) $C_{2-4}$ alkenyl,
(5) $C_{2-4}$ alkenyl substituted with CN,
(6) OH,
(7) O—$C_{1-4}$ alkyl,
(8) O—$C_{1-4}$ haloalkyl,
(9) halogen,
(10) CN,
(11) $NO_2$,
(12) $N(R^A)R^B$,
(13) $C(O)N(R^A)R^B$,
(14) $C(O)R^A$,
(15) $CO_2R^A$,
(16) $SR^A$,
(17) $S(O)R^A$,
(18) $SO_2R^A$,
(19) $SO_2N(R^A)R^B$,
(20) $SO_2N(R^A)C(O)R^B$, or
(21) CycQ; wherein:
each CycQ is $C_{3-7}$ cycloalkyl, wherein the cycloalkyl is optionally substituted with from 1 to 3 substituents, each of which is independently halogen, $C_{1-4}$ alkyl, OH, O—$C_{1-4}$ alkyl, $C_{1-4}$ haloalkyl, or O—$C_{1-4}$ haloalkyl;
$R^2$ and $R^3$ are each independently:
(1) H,
(2) $C_{1-4}$ alkyl,
(3) $C_{1-4}$ haloalkyl,
(4) $CH_2OH$,
(5) $CH_2O$—$C_{1-4}$ alkyl,
(6) $CH_2CN$,
(7) $CH_2N(R^A)R^B$,
(8) $CH_2C(O)N(R^A)R^B$,
(9) $CH_2C(O)R^A$,
(10) $CH_2CO_2R^A$,
(11) $CH_2S(O)_2R^A$,
(12) O—$C_{1-4}$ alkyl,
(13) O—$C_{1-4}$ haloalkyl,
(14) halogen,
(15) CN,
(16) $NO_2$,
(17) $N(R^AR^B)$,
(18) $C(O)N(R^A)R^B$,
(19) $C(O)R^A$,
(20) $C(O)$—$C_{1-4}$ haloalkyl,
(21) $C(O)OR^A$,
(22) $SR^A$,

(23) S(O)$_2$R$^A$,

(24) 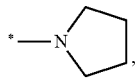

(25) 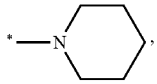

(26) 

(27) 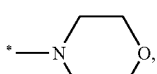

(28) 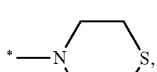

(29) 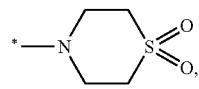

(30) 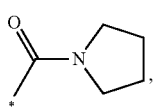

(31) 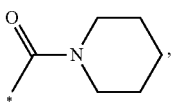

(32) 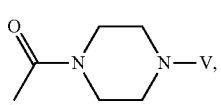

(33) 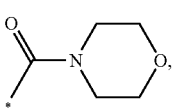

(34) 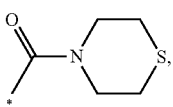

(35) 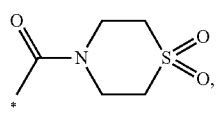

or
(36) C$_{3-7}$ cycloalkyl;
each V is independently H, CH$_3$, C(O)CH$_3$, C(O)OCH$_3$, or S(O)$_2$CH$_3$;
R$^5$ is H or C$_{1-4}$ alkyl;
each R$^A$ is independently H or C$_{1-4}$ alkyl; and
each R$^B$ is independently H or C$_{1-4}$ alkyl.

A first sub-class of the first class (alternatively referred to herein as "Sub-class C1-S1") includes compounds of Formula II and pharmaceutically acceptable salts thereof, wherein:

X$^1$ and X$^2$ are each independently:
(1) C$_{1-4}$ alkyl,
(2) C$_{1-4}$ haloalkyl,
(3) O—C$_{1-4}$ alkyl,
(4) halogen,
(5) CN,
(6) S—C$_{1-4}$ alkyl, or
(7) CycQ;
and provided that
(i) no more than one substituent is CycQ, and wherein CycQ is C$_{3-7}$ cycloalkyl; and
(ii) at least one of X$^1$ and X$^2$ is other than H;

R$^2$ is:
(1) C$_{1-4}$ alkyl,
(2) C$_{1-4}$ haloalkyl,
(3) O—C$_{1-4}$ alkyl,
(4) O—C$_{1-4}$ halooalkyl,
(5) halogen,
(6) S—C$_{1-4}$ alkyl, or
(7) C$_{3-7}$ cycloalkyl;

R$^3$ is:
(1) H,
(2) C$_{1-4}$ alkyl,
(3) C$_{1-4}$ haloalkyl,
(4) O—C$_{1-4}$ alkyl,
(5) O—C$_{1-4}$ haloalkyl,
(6) halogen,
(7) S—C$_{1-4}$ alkyl, or
(8) C$_{3-7}$ cycloalkyl; and R$^5$ is H or C$_{1-3}$ alkyl. In a feature of Sub-class C1-S1, all occurrences of C$_{1-4}$ haloalkyl are replaced with C$_{1-4}$ fluoroalkyl; all occurences of O—C$_{1-4}$ haloalkyl are replaced with O—C$_{1-4}$ fluoroalkyl; and all other variables are as originally defined in Sub-class C1-S1.

A second sub-class of the first class (Sub-class C1-S2) includes compounds of Formula II and pharmaceutically acceptable salts thereof, wherein:

X$^1$ and X$^2$ are each independently:
(1) Cl,
(2) Br,
(3) F,
(4) CN,
(5) CH$_3$,
(6) CHF$_2$,
(7) CF$_3$,
(8) OCH$_3$,
(9) SCH$_3$, or
(10) cyclopropyl, with the proviso that no more than one substituent is cyclopropyl.

R$^2$ is:
(1) CH$_3$,
(2) CF$_3$,
(3) CF$_2$CH$_3$,
(4) CH$_2$CF$_3$,
(5) OCH$_3$,
(6) OCF$_3$, (7) Cl,
(8) Br,
(9) F,
(10) SCH$_3$, or
(11) cyclopropyl;
R$^3$ is:
(1) H,
(2) CH$_3$,
(3) CF$_3$,
(4) CF$_2$CH$_3$,
(5) CH$_2$CF$_3$,
(6) OCH$_3$,
(7) OCF$_3$,
(8) Cl,
(9) Br,
(10) F,
(11) SCH$_3$, or
(12) cyclopropyl; and
R$^5$ is H, CH$^3$, or CH$_2$CH$_3$.

A second class of compounds of the present invention (Class C2) includes compounds of Formula III:

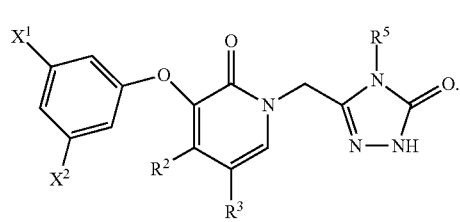

(III)

and pharmaceutically acceptable salts thereof, wherein the variables are as defined in Class C1.

A first sub-class of the second class (Sub-class C2-S1) includes compounds of Formula III and pharmaceutically acceptable salts thereof, wherein the variables are as defined in Sub-class C1-S1.

A second sub-class of the second class (Sub-class C2-S2) includes compounds of Formula III and pharmaceutically acceptable salts thereof, wherein the variables are as defined in Sub-class C1-S2.

A third sub-class of the second class (Sub-class C2-S3) includes compounds of Formula III and pharmaceutically acceptable salts thereof, wherein R$^3$ is H, Cl, Br or F; and the other variables are as defined in Class C2. In a feature of this sub-class, R$^3$ is H. In another feature of this sub-class, R$^5$ is CH$_3$ or CH$_2$CH$_3$. In still another feature of this sub-class, R$^3$ is H, and R$^5$ is CH$_3$ or CH$_2$CH$_3$.

A fourth sub-class of the second class (Sub-class C2-S4) includes compounds of Formula III and pharmaceutically acceptable salts thereof, wherein R$^3$ is H, Cl, Br or F; and the other variables are as defined in Sub-class C2-S1. In a feature of this sub-class, R$^3$ is H. In another feature of this sub-class, R$^5$ is CH$_3$ or CH$_2$CH$_3$. In still another feature of this sub-class, R$^3$ is H, and R$^5$ is CH$_3$ or CH$_2$CH$_3$.

A fifth sub-class of the second class (Sub-class C2-S5) includes compounds of Formula III and pharmaceutically acceptable salts thereof, wherein R$^3$ is H, Cl, Br or F; and the other variables are as defined in Sub-class C2-S2. In a feature of this sub-class, R$^3$ is H. In another feature of this sub-class, R$^5$ is CH$_3$ or CH$_2$CH$_3$. In still another feature of this sub-class, R$^3$ is H and R$^5$ is CH$_3$ or CH$_2$CH$_3$.

A forty-first embodiment of the present invention (Embodiment E41) is a compound of Formula I, or a pharmaceutically acceptable salt thereof, wherein the compound is selected from the group consisting of the title compounds set forth in Examples 1 to 8.

A forty-second embodiment of the present invention (Embodiment E42) is a compound of Formula I, or a pharmaceutically acceptable salt thereof, as originally defined or as defined in any of the foregoing embodiments, aspects, classes, sub-classes or features, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

The present invention also includes prodrugs of the compounds of Formula I. The term "prodrug" refers to a derivative of a compound of Formula I, or a pharmaceutically acceptable salt thereof, which is converted in vivo into Compound I. Prodrugs of compounds of Formula I can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). When the compound contains, for example, a hydroxy group, the prodrug can be a derivative of the hydroxy group such as an ester (—OC(O)R), a carbonate ester (—OC(O)OR), a phosphate ester (—O—P(=O)(OH)$_2$), or an ether (—OR). Other examples include the following: When the compound of Formula I contains a carboxylic acid group, the prodrug can be an ester or an amide, and when the compound of Formula I contains a primary amino group or another suitable nitrogen that can be derivatized, the prodrug can be an amide, carbamate, urea, imine, or a Mannich base. One or more functional groups in Compound I can be derivatized to provide a prodrug thereof. Conventional procedures for the selection and preparation of suitable prodrug derivatives are described, for example, in *Design of Prodrugs*, edited by H. Bundgaard, Elsevier, 1985; J. J. Hale et al., *J. Med. Chem.* 2000, vol. 43, pp. 1234-1241; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties.

Other embodiments of the present invention include the following:

(a) A pharmaceutical composition comprising an effective amount of a compound of Formula I as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a prodrug or pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, and HIV entry inhibitors.

(e) A combination which is (i) a compound of Formula I as defined above, or a prodrug or pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, and HIV entry inhibitors.

(g) A method for the inhibition of HIV reverse transcriptase in a subject in need thereof which comprises administering to the subject an effective amount of a compound of Formula I or a prodrug or pharmaceutically acceptable salt thereof.

(h) A method for the prophylaxis or treatment of infection by HIV (e.g., HIV-1) in a subject in need thereof which comprises administering to the subject an effective amount of a compound of Formula I or a prodrug or pharmaceutically acceptable salt thereof.

(i) The method of (h), wherein the compound of Formula I is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(j) A method for the prophylaxis, treatment or delay in the onset or progression of AIDS in a subject in need thereof which comprises administering to the subject an effective amount of a compound of Formula I or a prodrug or pharmaceutically acceptable salt thereof.

(k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I, or a prodrug or pharmaceutically acceptable salt thereof, (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes, subclasses, or features described above. In all of these embodiments etc., the compound may optionally be used in the form of a prodrug or pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its prodrug or salt and a pharmaceutically acceptable carrier and optionally one or more excipients, it is understood that the term "substantially pure" is in reference to a compound of Formula I or its prodrug or salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors and HIV-1 entry inhibitors.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_{2-6}$ alkenyl" (or "$C_2$-$C_6$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl). A class of alkenyls of interest with respect to the invention are alkenyls of formula —CH=CH—(CH$_2$)$_{1-3}$CH$_3$.

The term "alkynyl" refers to a monovalent straight or branched chain aliphatic hydrocarbon radical containing one carbon-carbon triple bond and having a number of carbon atoms in the specified range. Thus, for example, "C$_{2-6}$ alkynyl" (or "C$_2$-C$_6$ alkynyl") refers to all of the hexynyl and pentynyl isomers as well as 1-butynyl, 2-butynyl, 3-butynyl, 1-propynyl, 2-propynyl, and ethynyl.

The term "alkylene" refers to any divalent linear or branched chain aliphatic hydrocarbon radical having a number of carbon atoms in the specified range. Thus, for example, "—C$_{1-6}$ alkylene-" refers to any of the C$_1$ to C$_6$ linear or branched alkylenes, and "—C$_{1-4}$ alkylene-" refers to any of the C$_1$ to C$_4$ linear or branched alkylenes. A class of alkylenes of interest with respect to the invention is —(CH$_2$)$_{1-6}$-, and sub-classes of particular interest include —(CH$_2$)$_{1-4}$-, —(CH$_2$)$_{2-4}$-, —(CH$_2$)$_{1-3}$-, —(CH$_2$)$_{2-3}$-, —(CH$_2$)$_{1-2}$-, and —CH$_2$—. Another sub-class of interest is an alkylene selected from the group consisting of —CH$_2$—, —CH(CH$_3$)—, and —C(CH$_3$)$_2$-.

The term "cycloalkyl" refers to any monocyclic ring of an alkane having a number of carbon atoms in the specified range. Thus, for example, "C$_{3-8}$ cycloalkyl" (or "C$_3$-C$_8$ cycloalkyl") refers to cyclopropyl, cyclobutyl, cyclopentyl, cyclohexyl, cycloheptyl, and cyclooctyl.

The term "cycloalkenyl" refers to any monocyclic ring of an alkene having a number of carbon atoms in the specified range. Thus, for example, "C$_{5-8}$ cycloalkenyl" (or "C$_5$-C$_8$ cycloalkenyl") refers to cyclopentenyl, cyclohexenyl, cycloheptenyl, and cyclooctenyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "C$_{1-6}$ haloalkyl" (or "C$_1$-C$_6$ haloalkyl") refers to a C$_1$ to C$_6$ linear or branched alkyl group as defined above with one or more halogen substituents. The term "fluoroalkyl" has an analogous meaning except that the halogen substituents are restricted to fluoro. Suitable fluoroalkyls include the series (CH$_2$)$_{0-4}$CF$_3$ (i.e., trifluoromethyl, 2,2,2-trifluoroethyl, 3,3,3-trifluoro-n-propyl, etc.). A fluoroalkyl of particular interest is CF$_3$.

The term "C(O)" refers to carbonyl. The terms "S(O)$_2$" and "SO$_2$" each refer to sulfonyl. The term "S(O)" refers to sulfinyl.

An asterisk ("*") at the end of an open bond in a chemical group denotes the point of attachment of the group to the rest of the compound.

The term "aryl" refers to (i) phenyl, (ii) 9- or 10-membered bicyclic, fused carbocyclic ring systems in which at least one ring is aromatic, and (iii) 11- to 14-membered tricyclic, fused carbocyclic ring systems in which at least one ring is aromatic. Suitable aryls include, for example, phenyl, naphthyl, tetrahydronaphthyl (tetralinyl), indenyl, anthracenyl, and fluorenyl. A class of aryls of interest with respect to the invention is phenyl and napthyl. An aryl of particular interest is phenyl.

The term "heteroaryl" refers to (i) a 5- or 6-membered heteroaromatic ring containing from 1 to 4 heteroatoms independently selected from N, O and S, wherein each N is optionally in the form of an oxide, (ii) a 9- or 10-membered bicyclic fused ring system, wherein the fused ring system of (ii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5- (furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl

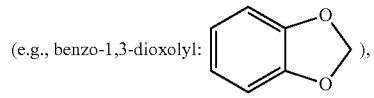

(e.g., benzo-1,3-dioxolyl: ), benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl

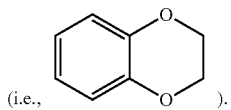

(i.e., ).

Examples of 4- to 7-membered, saturated heterocyclic rings within the scope of this invention (see, e.g., the definition of HetR) include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated, non-aromatic heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings and ring systems suitable for use in the present invention are not limited to those listed in the preceding paragraphs. These rings and ring systems are merely representative.

Unless expressly stated to the contrary in a particular context, any of the various cyclic rings and ring systems described herein may be attached to the rest of the compound at any ring atom (i.e., any carbon atom or any heteroatom) provided that the attachment is chemically allowed and a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3heteroatoms, 2 or 3 heteroatoms, 1 or 2 heteroatoms, 1 heteroatom, 2 heteroatoms, 3heteroatoms, and 4 heteroatoms. As another example, an aryl or heteroaryl described as optionally substituted with "from 1 to 6 substituents" is intended to include as aspects thereof, an aryl or heteroaryl substituted with 1 to 6 substituents, 2 to 6 substituents, 3 to 6 substituents, 4 to 6 substituents, 5 to 6 substituents, 6 substituents, 1 to 5 substituents, 2 to 5 substituents, 3 to 5substiuents, 4 to 5 substituents, 5 substituents, 1 to 4 substituents, 2 to 4 substituents, 3 to 4substituents, 4 substituents, 1 to 3 substituents, 2 to 3 substituents, 3 substituents, 1 to 2substituents, 2 substituents, and 1 substituent.

When any variable (e.g., $R^A$ or $R^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

As would be recognized by one of ordinary skill in the art, certain of the compounds of the present invention can exist as tautomers. All tautomeric forms of these compounds, whether isolated individually or in mixtures, are within the scope of the present invention. For example, in instances where an oxo (=O) substituent is permitted on a heteroaromatic ring and keto-enol tautomerism is possible, it is understood that the substituent might in fact be present, in whole or in part, in the hydroxy form, as exemplified here:

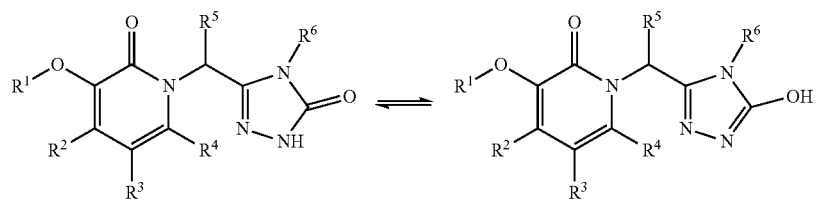

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

As a result of the selection of substituents and substituent patterns, certain compounds of the present invention can have asymmetric centers and can occur as mixtures of stereoisomers, or as individual diastereomers, or enantiomers. All isomeric forms of these compounds, whether individually or in mixtures, are within the scope of the present invention.

The atoms in a compound of Formula I may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The methods of the present invention involve the use of compounds of the present invention in the inhibition of HIV reverse transcriptase (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Preventing AIDS, treating AIDS, delaying the onset or progression of AIDS, or treating or preventing infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery. As another example, the present invention can also be employed to prevent transmission of HIV from a pregnant female infected with HIV to her unborn child or from an HIV-infected female who is nursing (i.e., breast feeding) a child to the child via administration of an effective amount of Compound I or a prodrug or pharmaceutically acceptable salt thereof.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of Formula I mean providing the compound or a prodrug of the compound to the individual in need of treatment or prophylaxis. When a compound or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

Ingredients suitable for inclusion in a pharmaceutical composition are pharmaceutically acceptable ingredients, which means the ingredients must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV reverse transcriptase (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the method of the present invention (i.e., inhibiting HIV reverse transcriptase, treating or prophylaxis of HIV infection or treating, prophylaxis of, or delaying the onset or progression of AIDS), the compounds of Formula I, optionally in the form of a salt or a prodrug, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125, Intelence ® | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ™ | InI |
| ritonavir, Norvir ® | PI |
| saquinavir, Invirase ®, Fortovase ® | PI |
| stavudine, d4T,didehydrodeoxythymidine, Zerit ® | nRTI |
| tenofovir DF (DF = disoproxil fumarate), TDF, Viread ® | nRTI |
| tipranavir, Aptivus ® | PI |
| vicriviroc | EI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in editions of the *Physicians' Desk Reference*, such as the 63rd edition (2009) and earlier editions. The dosage ranges for a compound of the invention in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition. Thus the compounds of this invention are commercial products to be sold for these purposes.

Abbreviations employed herein include the following:
AcOH=acetic acid;
BrdUTP=bromodeoxyuridine triphosphate;
BSA=bovine serum albumin;
CHAPS=3[(3-cholamidopropyl)dimethylammonio]-propanesulfonic acid;
DMF=dimethylformamide;
DMSO=dimethyl sulfoxide;
dNTP=deoxynucleoside triphosphate;
EDTA=ethylenediaminetetraacetic acid;
EGTA=ethylene glycol bis(2-aminoethyl ether)-N,N,N',N'-tetraacetic acid;
Et=ethyl;
EtOAc=ethyl acetate;
EtOH=ethanol;
FBS=fetal bovine serum;
HIV=human immunodeficiency virus;
HPLC=high performance liquid chromatography;
LCAP=liquid chromatography area percent
LC-MS=liquid chromatography-mass spectroscopy;
Me=methyl;
MeOH=methanol;
Me-THF=2-methyltetrahydrofuran;
NBS=N-bromosuccinimide;
NHS=normal human serum;
NMP=N-methyl pyrrolidinone;
NMR=nuclear magnetic resonance;
PBS=phosphate buffered saline;
$S_NAr$=nucleophilic aromatic substitution;
t-BuOH=tert-butanol;
THF=tetrahydrofuran;
TFAA=trifluoroacetic anhydride.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme I depicts a method for preparing compounds of Formula I in which hydroxypyridine I-1 is alkylated with chlorotriazolinone I-2 to provide I-3 which can be selectively alkylated with an alkyl halide (e.g., methyl iodide, ethyl iodide, etc.) to afford the desired I-4.

Scheme I

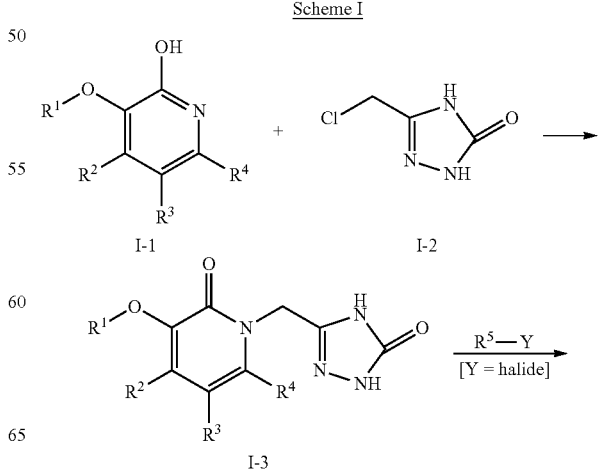

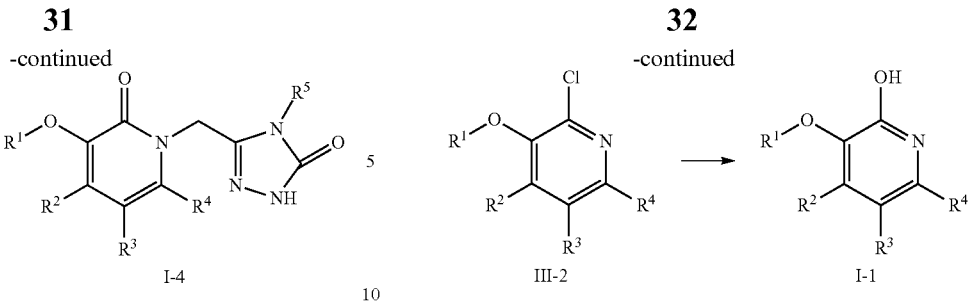

Scheme II depicts an alternative route to compounds of the present invention, wherein fluorohydroxypyridine II-1 can be alkylated with chlorotriazolinone II-2 to provide the alkylated product II-3 which can be converted to the desired II-5 via nucleophilic aromatic substitution ($S_NAr$) using a suitable hydroxyarene II-4.

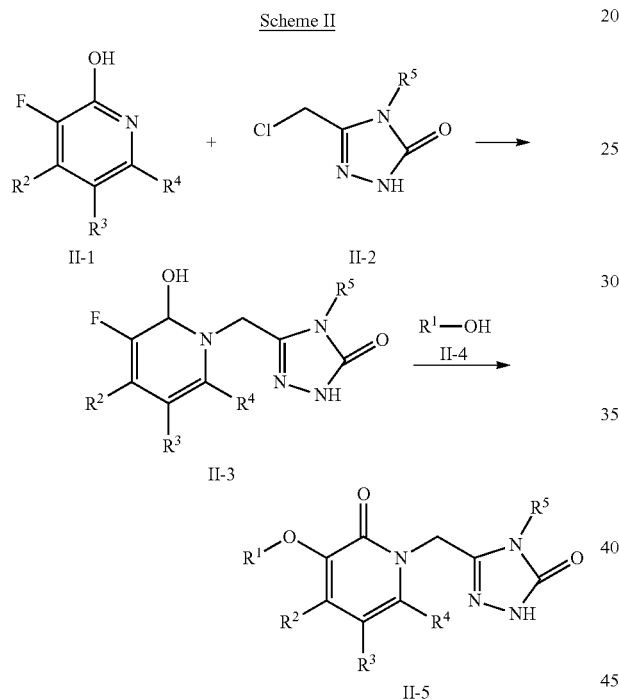

Hydroxypyridines of formula I-1 (Scheme 1) can be prepared in accordance with Scheme III, wherein a $S_NAr$ reaction between pyridine III-1 (such as commercially available 2-chloro-3-fluoro-4-(trifluoromethyl)pyridine) and hydroxyarene II-4 can provide chloropyridine III-2, which can be hydrolyzed under basic conditions to the hydroxypyridine I-1.

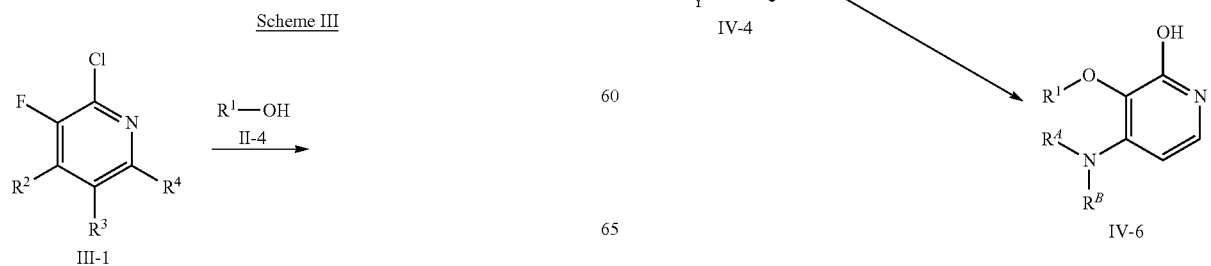

Another method for preparing hydroxypyridines of formula I-1 is exemplified in Scheme IV, wherein $S_NAr$ coupling of commercially available 2-chloro-3-fluoro-4-nitropyridone-N-oxide IV-1 with a suitable hydroxyarene II-4 provides N-oxide IV-2, which can first be converted to dihalides IV-3 and then hydrolyzed to hydroxypyridine IV-4. Further derivatization of hydroxypyridine IV-4 is possible through transition metal-catalyzed coupling processes, such as Stille or boronic acid couplings using a $PdL_n$ catalyst (wherein L is a ligand such as triphenylphosphine, tri-tert-butylphosphine or xantphos) to form hydroxypyridines IV-5, or amination chemistry to form hydroxypyridines IV-6 in which $R^2$ is $N(R^A)R^B$.

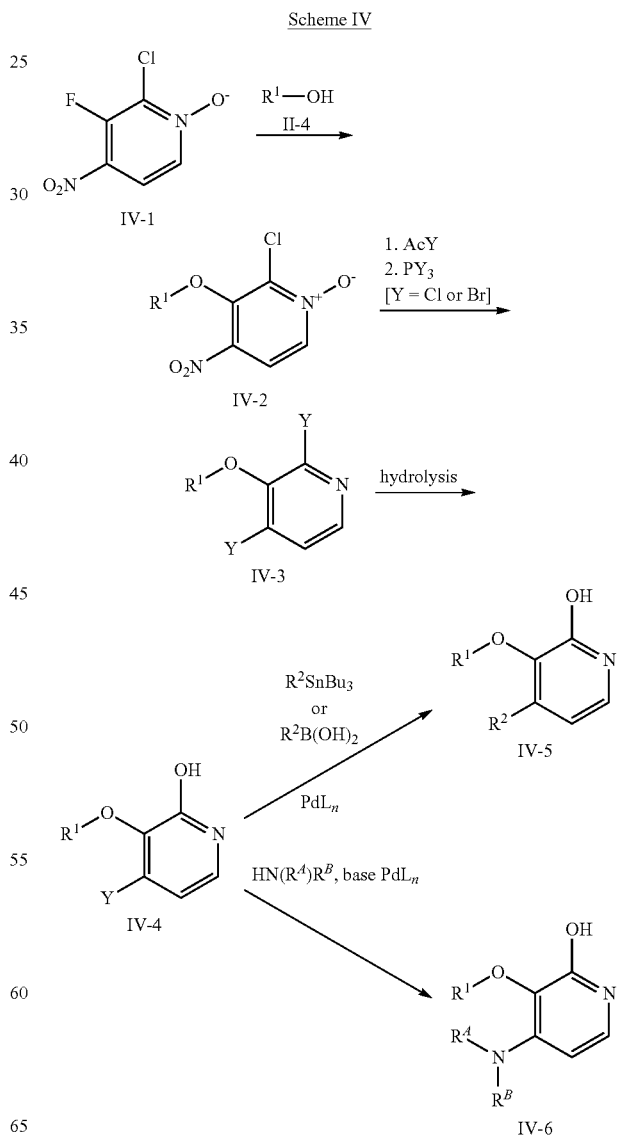

Scheme V depicts the introduction of substitution at the five-position of the hydroxypyridines via bromination, and subsequent transition metal-catalyzed chemistries, such as Stille or boronic acid couplings using PdL$_n$ in which L is as defined in Scheme IV to form hydroxypyridines V-3, or amination chemistry to form hydroxypyridines V-4 in which R$^3$ is N(R$^A$)R$^B$.

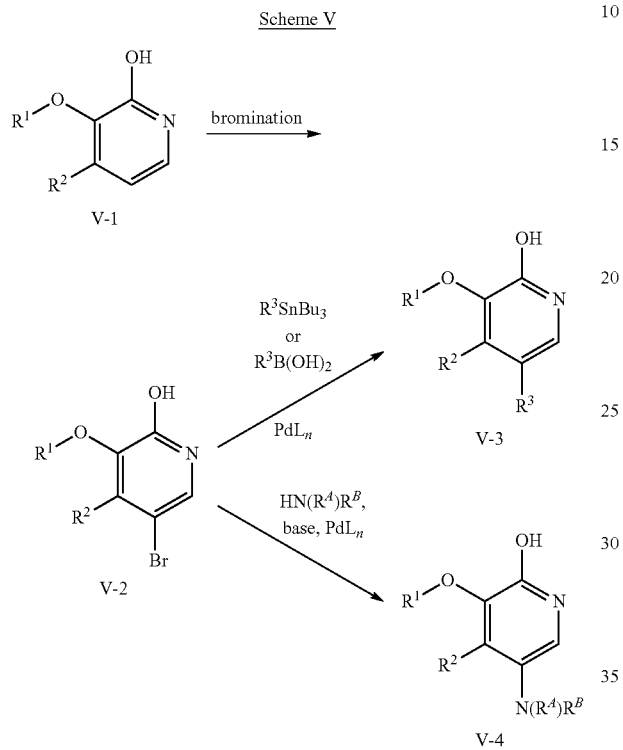

As shown in Scheme IV, fluorohydroxypyridines II-1 (Scheme II) are available from the commercially available 3-fluoropyridines VI-1 through N-oxide formation and rearrangement as described in Konno et al., *Heterocycles* 1986, vol. 24, p. 2169.

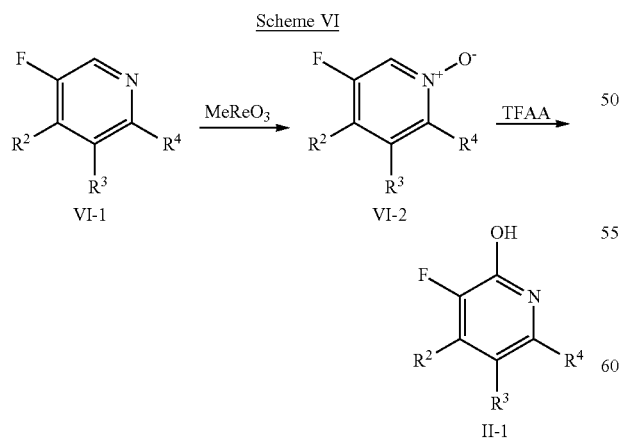

The following examples serve only to illustrate the invention and its practice. The examples are not to be construed as limitations on the scope or spirit of the invention.

The term "room temperature" in the examples refers to the ambient temperature which was typically in the range of about 20° C. to about 26° C.

EXAMPLE 1

3-Chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile (1-1)

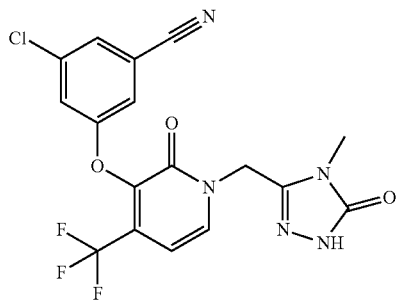 [SMILES: Cn1c(Cn2ccc(C(F)(F)F)c(Oc3cc(Cl)cc(C#N)c3)c2=O)n[nH]c1=O]

Step 1(a): 3-(3-bromo-5-chlorophenoxy)-2-chloro-4-(trifluoromethyl)pyridine (1-2)

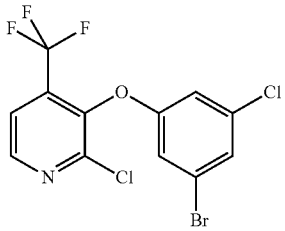 [SMILES: FC(F)(F)c1ccnc(Cl)c1Oc1cc(Cl)cc(Br)c1]

A mixture of the 3-bromo-5-chlorophenol (3.74 g; 18.0 mmol), 2-chloro-3-fluoro-4-(trifluoromethyl)pyridine (3.00 g; 15.0 mmol) and K$_2$CO$_3$ (2.49 g; 18.0 mmol) in NMP (15 mL) was heated to 120° C. for one hour, then cooled to room temperature. The mixture was then diluted with 250 mL EtOAc and washed with 3×250 mL 1:1 H$_2$O:brine. The organic extracts were dried (Na$_2$SO$_4$) and concentrated in vacuo. Purification by ISCO CombiFlash (120 g column; load with toluene; 100:0 to 0:100 hexanes:CH$_2$Cl$_2$ over 40 minutes) provided title compound (1-2) as a white solid. Repurification of the mixed fractions provided additional title compound. $^1$H NMR (400 MHz, CDCl$_3$): δ 8.55 (d, J=5.0 Hz, 1 H); 7.64 (d, J=5.0 Hz, 1 H); 7.30 (s, 1 H); 6.88 (s, 1 H); 6.77 (s, 1 H).

Step 1(b): 3-(3-bromo-5-chlorophenoxy)-4-(trifluoromethyl)pyridin-2-ol (1-3)

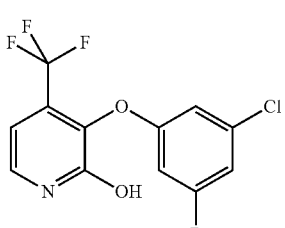

To a suspension of 3-(3-bromo-5-chlorophenoxy)-2-chloro-4-(trifluoromethyl)pyridine (1-2; 3.48 g; 8.99 mmol) in 'BuOH (36 mL) was added KOH (1.51 g; 27.0 mmol) and the mixture was heated to 75° C. overnight, at which point a yellow oily solid had precipitated from solution, and LCMS analysis indicated complete conversion. The mixture was cooled to room temperature, and neutralized by the addition of ~50 mL saturated aqueous $NH_4Cl$. The mixture was diluted with 50 mL $H_2O$, then extracted with 2×100 mL EtOAc. The combined organic extracts were dried ($Na_2SO_4$) and concentrated in vacuo. Purification by ISCO CombiFlash (120 g column; dry load; 100:0 to 90:10 $CH_2Cl_2$:MeOH over 40 minutes) provided the title compound (1-3) as a fluffy white solid. $^1H$ NMR (400 MHz, DMSO): δ 12.69 (s, 1 H); 7.59 (d, J=6.9 Hz, 1 H); 7.43 (t, J=1.7 Hz, 1 H); 7.20 (t, J=1.9 Hz, 1 H); 7.13 (t, J=2.0 Hz, 1 H); 6.48 (d, J=6.9 Hz, 1 H).

Step 1(c): 3-chloro-5-{[2-hydroxy-4-(trifluoromethyl)pyridin-3-yl]oxy}benzonitrile (1-4)

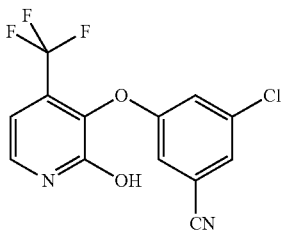 [SMILES: N#Cc1cc(Cl)cc(Oc2c(C(F)(F)F)ccnc2O)c1]

To a suspension of 3-(3-bromo-5-chlorophenoxy)-4-(trifluoromethyl)pyridin-2-ol (1-3; 3.25 g; 8.82 mmol) in NMP (29 mL) was added CuCN (7.90 g; 88 mmol) and the mixture was heated to 175° C. for 5 hours, then cooled to room temperature slowly. With increased fumehood ventilation, 100 mL glacial AcOH was added, then 100 mL EtOAc and the mixture was filtered through Celite (EtOAc rinse). The filtrate was washed with 3×200 mL 1:1 $H_2O$:brine, then the organic extracts were dried ($Na_2SO_4$) and concentrated in vacuo. Purification by ISCO CombiFlash (120 g column; dry load; 100:0 to 90:10 $CH_2Cl_2$:MeOH over 40 minutes), then trituration of the derived solid with $Et_2O$ (to remove residual NMP which had co-eluted with the product) provided the title compound (1-4). $^1H$ NMR (400 MHz, DMSO): δ 12.71 (s, 1 H); 7.75 (s, 1 H); 7.63-7.57 (m, 2 H); 7.54 (s, 1 H); 6.49 (d, J=6.9 Hz, 1 H).

Step 1(d): 5-(chloromethyl)-2,4-dihydro-3H-1,2,4-triazol-3-one (1-5)

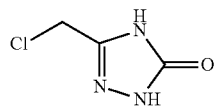

The title compound was prepared as described in the literature: Cowden, C. J.; Wilson, R. D.; Bishop, B. C; Cottrell, I. F.; Davies, A. J.; Dolling, U.-H. *Tetrahedron Lett.* 2000, 41, 8661.

Step 1(e): 3-chloro-5-({2-oxo-1-[(5-oxo-4,5-dihydro-1H-1,2,4-triazol-3-yl)methyl]-4-(trifluoromethyl)-1,2-dihydropyridin-3-yl}oxy)benzonitrile (1-6)

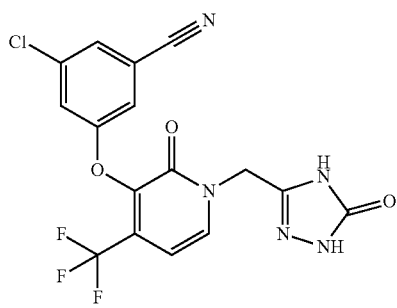 [SMILES: N#Cc1cc(Cl)cc(Oc2c(C(F)(F)F)ccn(Cc3n[nH]c(=O)[nH]3)c2=O)c1]

A suspension of the 3-chloro-5-{[2-hydroxy-4-(trifluoromethyl)pyridin-3-yl]oxy}benzonitrile (1-4; 2.00 g; 6.36 mmol), 5-(chloromethyl)-2,4-dihydro-3H-1,2,4-triazol-3-one (1-5; 0.849 g; 6.36 mmol) and $K_2CO_3$ (0.878 g; 6.36 mmol) in DMF (32 mL) was stirred for 2 hours at room temperature, at which point LCMS analysis indicated complete conversion. The mixture was diluted with 200 mL Me-THF and washed with 150 mL 1:1:1 $H_2O$:brine:saturated aqueous $NH_4Cl$, then further washed with 2×150 mL 1:1 $H_2O$:brine. The aqueous fractions were further extracted with 150 mL Me-THF, then the combined organic extracts were dried ($Na_2SO_4$) and concentrated in vacuo. Purification by ISCO CombiFlash (80 g column; dry load; 100:0 to 90:10 EtOAc:EtOH over 25 minutes) provided the title compound (1-6) as a white solid. $^1HNMR$ (400 MHz, DMSO): δ 11.46 (s, 1 H); 11.39 (s, 1 H); 7.93 (d, J=7.3 Hz, 1 H); 7.76 (s, 1 H); 7.58 (s, 1 H); 7.51 (s, 1 H); 6.67 (d, J=7.3 Hz, 1 H); 5.02 (s, 2 H).

Step 1(f): 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile (1-1)

A solution of 3-chloro-5-({2-oxo-1-[(5-oxo-4,5-dihydro-1H-1,2,4-triazol-3-yl)methyl]-4-(trifluoromethyl)-1,2-dihydropyridin-3-yl}oxy)benzonitrile (1-6; 2.37 g; 5.76 mmol) and $K_2CO_3$ (0.796 g; 5.76 mmol) in DMF (58 mL) was cooled to 0° C., then methyl iodide (0.360 mL; 5.76 mmol) was added. The mixture was allowed to warm to room temperature, and stirred for 90 minutes, at which point LCMS analysis indicated >95% conversion, and the desired product of ~75% LCAP purity, with the remainder being unreacted starting material and bis-methylation products. The mixture was diluted with 200 mL Me-THF, and washed with 3×200 mL 1:1 $H_2O$:brine. The aqueous fractions were further extracted with 200 mL Me-THF, then the combined organic extracts were dried ($Na_2SO_4$) and concentrated in vacuo. The resulting white solid was first triturated with 100 mL EtOAc, then with 50 mL THF, which provided (after drying) the title compound (1-1) of >95% LCAP. Purification to >99% LCAP is possible using Prep LCMS (Max-RP, 100×30 mm column; 30-60% $CH_3CN$ in 0.6% aqueous HCOOH over 8.3 min; 25 mL/min). $^1H$ NMR (400 MHz, DMSO): δ 11.69 (s, 1 H); 7.88 (d, J=7.3 Hz, 1 H); 7.75 (s, 1 H); 7.62 (s, 1 H); 7.54 (s, 1 H); 6.67 (d, J=7.3 Hz, 1 H); 5.17 (s, 2 H); 3.11 (s, 3 H).

EXAMPLE 1A

3-Chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile (1-1)

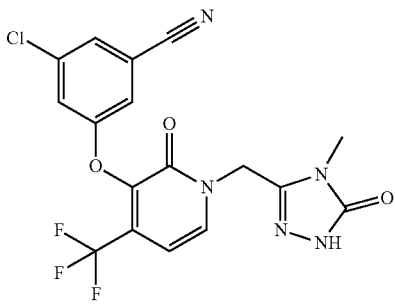 [SMILES: Cn1c(Cn2ccc(C(F)(F)F)c(Oc3cc(Cl)cc(C#N)c3)c2=O)n[nH]c1=O]

Step 1A(a): 2-chloro-3-(3-chloro-5-iodophenoxy)-4-(trifluoromethyl)pyridine (1A-2)

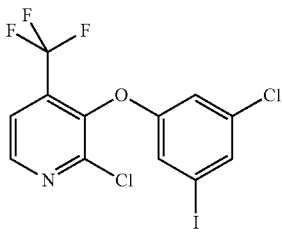 [SMILES: FC(F)(F)c1ccnc(Cl)c1Oc1cc(Cl)cc(I)c1]

A mixture of the 3-chloro-1-iodophenol (208 g; 816.0 mmol), 2-chloro-3-fluoro-4-(trifluoromethyl)pyridine (155 g; 777.0 mmol) and $K_2CO_3$ (161 g; 1165.0 mmol) in NMP (1.5 L) was held at 60° C. for 2.5 hours, and then left at room temperature for 2 days. The mixture was then re-heated to 60° C. for 3 hours, then cooled to room temperature. The mixture was then diluted with 4 L EtOAc and washed with 2 L water+1 L brine. The combined organics were then washed 2× with 500 mL half brine then 500 mL brine, dried over $MgSO_4$ and concentrated to afford crude 1A-2. $^1H$ NMR (500 MHz, DMSO) δ 8.67 (d, J=5.0 Hz, 1 H), 7.98 (d, J=5.0 Hz, 1 H), 7.63-7.62 (m, 1 H), 7.42-7.40 (m, 1 H), 7.22 (t, J=2.1 Hz, 1 H).

Step 1A(b): 2-chloro-3-(3-chloro-5-iodophenoxy)-4-(trifluoromethyl)pyridine (1A-3)

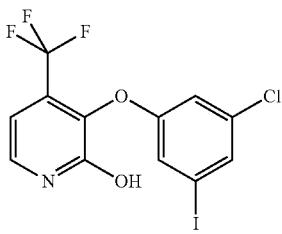 [SMILES: Oc1nccc(C(F)(F)F)c1Oc1cc(Cl)cc(I)c1]

To a suspension of 3-(3-chloro-5-iodophenoxy)-2-chloro-4-(trifluoromethyl)pyridine (1A-2; 421 g, 970 mmol) in t-BuOH (1 L) was added KOH (272 g, 4850 mmol) and the mixture was heated to 75° C. for 1 hour, at which point HPLC analysis indicated >95% conversion. The t-BuOH was evaporated and the mixture diluted with water (7 mL/g, 2.4 L) and then cooled to 0° C., after which 12N HCl (~240 mL) was added until pH 5. This mixture was then extracted with EtOAc (20 mL/g, 6.5 L), back extracted with EtOAc 1×5 mL/g (1.5 L), washed 1× water:brine 1:1 (10 mL/g, 3.2 L), 1× brine (10 mL/g, 3.2 L), dried over $MgSO_4$, filtered and concentrated to afford a crude proudct. The crude product was suspended in MTBE (2.25 L, 7 mL/g), after which hexanes (1 L, 3 mL/g) was added to the suspension over ten minutes, and the mixturen was aged 30 minutes at room temperature. The product was filtered on a Buchner, rinsed with MTBE/hexanes 1:2 (2 mL/g=640 mL), then hexanes (640 mL), and dried on frit to afford 1A-3. $^1H$ NMR (400 MHz, acetone-d6): δ 11.52 (s, 1 H); 7.63 (d, J=7.01 Hz, 1 H); 7.50-7.48 (m, 1 H); 7.34-7.32 (m, 1 H); 7.09-7.07 (m, 1 H); 6.48 (d, J=7.01 Hz, 1 H).

Step 1A(c): 3-chloro-5-{[2-hydroxy-4-(trifluoromethyl)pyridin-3-yl]oxy}benzonitrile (1-4)

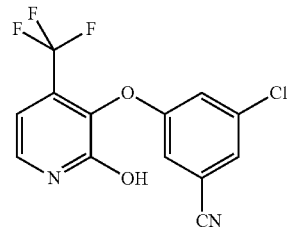 [SMILES: N#Cc1cc(Cl)cc(Oc2c(C(F)(F)F)ccnc2O)c1]

A solution of 3-(3-chloro-5-iodophenoxy)-4-(trifluoromethyl)pyridin-2-ol (1A-3; 190 g; 457 mmol) in DMF (914 mL) was degassed for 20 minutes by bubbling $N_2$, after which CuCN (73.7 g; 823 mmol) was added, and then the mixture was degassed an additional 5 minutes. The mixture was then heated to 120° C. for 17 hours, then cooled to room temperature and partitioned between 6 L MeTHF and 2 L ammonium buffer (4:3:1=$NH_4Cl$ sat/water/$NH_4OH$ 30%). The organic layer washed with 2 L buffer, 1 L buffer and 1 L brine then, dried over $MgSO_4$ and concentrated. The crude solid was then stirred in 2.2 L of refluxing MeCN for 45 minutes, then cooled in a bath to room temperature over 1 hour, aged 30 minutes, then filtered and rinsed with cold MeCN (2×400 mL). The solid was dried on frit under $N_2$ arm for 60 hours to afford title compound 1-4. $^1H$ NMR (400 MHz, DMSO): δ 12.71 (s, 1 H); 7.75 (s, 1 H); 7.63-7.57 (m, 2 H); 7.54 (s, 1 H); 6.49 (d, J=6.9 Hz, 1 H).

Steps 1A(d) and 1A(e)

The title compound 1-1 was then prepared from compound 1-4 using procedures similar to those described in Steps 1(d) and 1(e) set forth above in Example 1.

EXAMPLE 2

3-Chloro-5-({1-[(4-ethyl-5-oxo-4,5-dihydro-1H-1,2,4-triazol-3-yl)methyl]-2-oxo-4-(trifluoromethyl)-1,2-dihydropyridin-3-yl}oxy)benzonitrile (2-1)

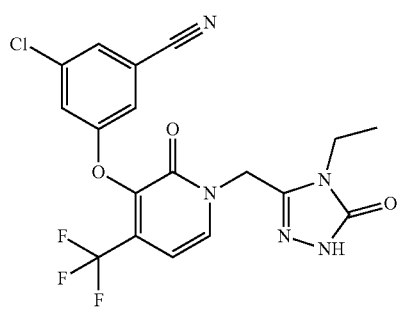 [SMILES: CCn1c(Cn2ccc(C(F)(F)F)c(Oc3cc(Cl)cc(C#N)c3)c2=O)n[nH]c1=O]

The title compound was prepared using the procedure described in Example, wherein the iodomethane employed in Step 1(f) was replaced with iodoethane. ¹H NMR (400 MHz, DMSO): δ 11.68 (s, 1 H); 7.92 (d, J=7.3 Hz, 1 H); 7.76 (s, 1 H); 7.60 (s, 1 H); 7.52 (s, 1 H); 6.69 (d, J=7.3 Hz, 1 H); 5.20 (s, 2 H); 3.65-3.56 (m, 2 H); 1.11 (t, J=7.1 Hz, 3 H).

EXAMPLE 3

3-Chloro-5-({4-chloro-1-[(4-methyl-5-oxo-4,5-dihydro-1H-1,2,4-triazol-3-yl)methyl]-2-oxo-1,2-dihydropyridin-3-yl}oxy)benzonitrile (3-1)

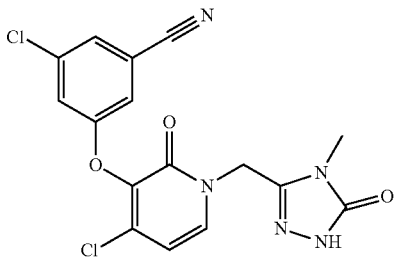 [SMILES: Cn1c(Cn2ccc(Cl)c(Oc3cc(Cl)cc(C#N)c3)c2=O)n[nH]c1=O]

Step 3(a): 3-(3-bromo-5-chlorophenoxy)-2-chloro-4-nitropyridine 1-oxide (3-2)

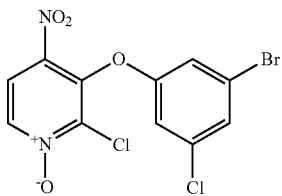

A suspension of 3-bromo-5-chlorophenol (1.32 g; 6.35 mmol), 2-chloro-3-fluoro-4-nitropyridone-N-oxide (1.11 g; 5.78 mmol) and K₂CO₃ (0.798 g; 5.78 mmol) in 3:1 THF: DMF (23 mL) was stirred at room temperature for 5 hours. THF was removed in vacuo, and then the mixture was diluted with saturated aqueous NaHCO₃ and extracted three times with EtOAc. The combined organic extracts were washed with brine, dried (MgSO₄) and concentrated in vacuo. The resulting residue was triturated with Et₂O to provide the title compound as a brown solid of sufficient purity to be used directly. ¹H NMR (400 MHz, MeOD): δ 8.57 (d, J=7.5 Hz, 1 H); 8.21 (d, J=7.5 Hz, 1 H); 7.43 (s, 1 H); 7.26 (s, 1 H); 7.16 (s, 1 H).

Step 3(b): 3-(3-bromo-5-chlorophenoxy)-2,4-dichloropyridine (3-3)

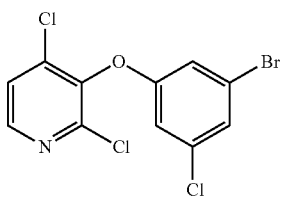 [SMILES: Clc1cc(Br)cc(Oc2c(Cl)ccnc2Cl)c1]

A suspension of 3-(3-bromo-5-chlorophenoxy)-2-chloro-4-nitropyridine 1-oxide (3-2; 1.41 g; 3.71 mmol) in AcOH (37 mL) was heated to 60° C., and then acetyl chloride (2.64 mL; 37.1 mmol) was added. After 60 minutes at 60° C., the mixture was cooled to room temperature, and AcOH was removed in vacuo. The residue was diluted with saturated aqueous NaHCO₃ and extracted three times with EtOAc. The combined organic extracts were washed with brine, dried (MgSO₄) and concentrated in vacuo. The resulting orange oil was diluted with CHCl₃ (37 mL), cooled to 0° C., then PCl₃ (4.87 mL; 55.7 mmol) was added. The mixture was heated to 60° C. overnight, then cooled to room temperature and quenched by careful addition of saturated aqueous NaHCO₃ until the aqueous layer was alkaline. The mixture was extracted three times with CH₂Cl₂, then the combined extracts were washed with brine, dried (MgSO₄) and concentrated in vacuo to provide title compound as a white solid of sufficient purity to be used directly.
¹H NMR (400 MHz, MeOD): δ 8.32 (d, J=5.3 Hz, 1 H); 7.68 (d, J=5.3 Hz, 1 H); 7.38 (s, 1 H); 7.02 (s, 1 H); 6.95-6.90 (m, 1 H).

Step 3(c) 3-(3-bromo-5-chlorophenoxy)-4-chloropyridin-2-ol (3-4)

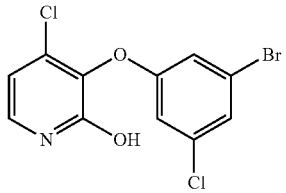 [SMILES: Oc1nccc(Cl)c1Oc1cc(Cl)cc(Br)c1]

To a solution of 3-(3-bromo-5-chlorophenoxy)-2,4-dichloropyridine (3-3; 81 mg; 0.23 mmol) in t-BuOH (1.0 mL) was added KOH (39 mg; 0.69 mmol) and the mixture was heated to 75° C. overnight. After cooling to room temperature, the mixture was diluted with water, and extracted with EtOAc. The organic phase was washed with brine, dried (MgSO₄) and concentrated in vacuo. Purification by ISCO CombiFlash (4 g column; dry load; 100:0 to 20:80 hexanes:EtOAc) provided the title compound. ¹H NMR (400 MHz, CDCl₃): δ 12.86 (s, 1 H); 7.27-7.23 (m, 2 H); 7.02 (s, 1 H); 6.91 (s, 1 H); 6.45 (d, J=7.1 Hz, 1 H).

Step 3(d): 3-chloro-5-[(4-chloro-2-hydroxypyridin-3-yl)oxy]benzonitrile (3-5)

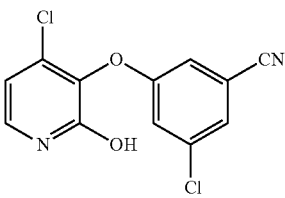

A solution of 3-(3-bromo-5-chlorophenoxy)-4-chloropyridin-2-ol (3-4; 205 mg; 0.612 mmol) in DMF was degassed with N₂ for 5 minutes, then Zn(CN)₂ (71.9 mg; 0.612 mmol) and Pd(PPh₃)₄ (106 mg; 0.092 mmol) were added. The mixture was heated to 90° C. for 2 hours, then cooled to room temperature. The mixture was diluted with EtOAc and water, resulting in precipitation of the desired compound which was collected by filtration. Further washing with water, EtOAc, CH₂Cl₂ and MeOH provided the title compound as a white solid. ¹HNMR (400 MHz, MeOD): δ 7.52 (s, 1 H); 7.43 (d, J=7.1 Hz, 1 H); 7.29 (s, 1 H); 7.27 (s, 1 H); 6.58 (d, J=7.1 Hz, 1 H).

Steps 3(e) and (f): 3-chloro-5-({4-chloro-1-[(4-methyl-5-oxo-4,5-dihydro-1H-1,2,4-triazol-3-yl)methyl]-2-oxo-1,2-dihydropyridin-3-yl}oxy)benzonitrile (3-1)

The title compound was prepared using modifications of Steps 1(e) and (f), replacing 3-chloro-5-{[2-hydroxy-4-(trifluoromethyl)pyridin-3-yl]oxy}benzonitrile (1-4) in Step 1(e) with 3-chloro-5-[(4-chloro-2-hydroxypyridin-3-yl)oxy]benzonitrile (3-5). ¹H NMR (400 MHz, DMSO): δ 11.66 (s, 1 H); 7.72 (t, J=3.5 Hz, 2 H); 7.53 (s, 1 H); 7.44 (s, 1 H); 6.62 (d, J=7.5 Hz, 1 H); 5.10 (s, 2 H); 3.11 (s, 3 H).

EXAMPLE 4

3-({4-Bromo-1-[(4-methyl-5-oxo-4,5-dihydro-1H-1,2,4-triazol-3-yl)methyl]-2-oxo-1,2-dihydropyridin-3-yl}oxy)-5-chlorobenzonitrile (4-1)

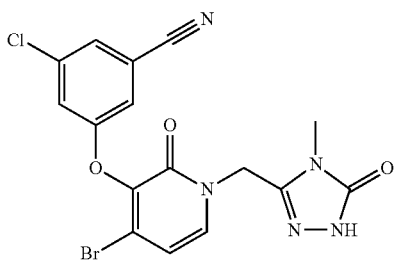 [SMILES: Cn1c(Cn2ccc(Br)c(Oc3cc(Cl)cc(C#N)c3)c2=O)n[nH]c1=O]

Step 4(a): 3-chloro-5-iodo-phenol (4-2)

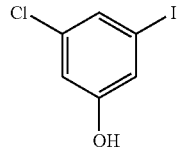

A solution of 1-chloro-3-iodobenzene (5.00 g; 21.0 mmol) in hexanes (70 mL) was purged with N₂ for 5 minutes. Bis-(pinacolato)borane (6.39 g; 25.2 mmol), di-μ-methoxo-bis-(1,5-cyclooctadiene)diiridium(I) (0.208 g; 0.315 mmol) and 4,4-di-tert-butyl-2,2-dipyridyl (0.169 g; 0.629 mmol) were added and the reaction was stirred overnight at room temperature. Hexanes were removed in vacuo, then the residue was rediluted with acetone (70 mL) and Oxone® (i.e., potassium peroxymonosulfate) (12.9 g; 21.0 mmol) in water (70 mL) was added. After stirring for 10 minutes, the reaction was quenched by the addition of aqueous 5% Na₂SO₃, and the product was extracted three times with Et₂O. The combined organic extracts were dried (MgSO₄) and concentrated in vacuo. Purification by ISCO CombiFlash (100:0 to 70:30 hexanes:EtOAc) provided the title compound as a brown oil. ¹H NMR (400 MHz, CDCl₃): δ 7.29 (s, 1 H); 7.13 (s, 1 H); 6.89-6.80 (m, 1 H); 5.91 (s, 1 H).

Step 4(b): 2-chloro-3-(3-chloro-5-iodophenoxy)-4-nitropyridine 1-oxide (4-3)

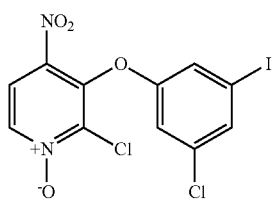

A suspension of 3-chloro-5-iodo-phenol (4-2; 5.00 g; 19.7 mmol), 2-chloro-3-fluoro-4-nitropyridone-N-oxide (3.67; 19.1 mmol) and K₂CO₃ (2.72 g; 19.7 mmol) in THF (79 mL) was stirred at room temperature for overnight. The mixture was concentrated in vacuo, then diluted with aqueous saturated. NaHCO₃ and extracted with CH₂Cl₂. The organic extracts were dried (MgSO₄) and concentrated in vacuo. The resulting residue was triturated with Et₂O to provide the title compound as a yellow solid of sufficient purity to be used directly. ¹H NMR (400 MHz, CDCl₃): δ 8.40 (d, J=7.4 Hz, 1 H); 8.04 (d, J=7.4 Hz, 1 H); 7.54 (s, 1 H); 7.12 (s, 1 H); 6.88 (t, J=2.0 Hz, 1 H).

Step 4(c): 2,4-dibromo-3-(3-chloro-5-iodophenoxy)pyridine (4-4)

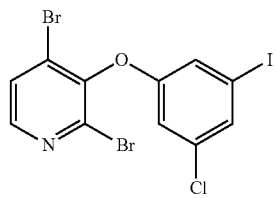 [SMILES: Clc1cc(I)cc(Oc2c(Br)ccnc2Br)c1]

A suspension of 2-chloro-3-(3-chloro-5-iodophenoxy)-4-nitropyridine 1-oxide (4-3; 3.00 g; 7.03 mmol) in AcOH (23 mL) was heated to 80° C., then acetyl bromide (5.19 mL; 70.3 mmol) was added. After 4 hours at 60° C., the mixture was cooled to room temperature, and AcOH was removed in vacuo. The residue was diluted with aqueous saturated NaHCO₃ and extracted three times with CH₂Cl₂. The combined organic extracts were dried (MgSO₄) and concentrated in vacuo. The resulting residue was diluted with CHCl₃ (23 mL) then PBr₃ (9.94 mL; 105 mmol) was added. The mixture was heated to 80° C. overnight, then cooled to room temperature the poured onto ice and neutralized by the slow addition of 1 M NaOH(aq). The mixture was extracted three times with CH₂Cl₂, leaving a cloudy organic layer. The solvent was removed in vacuo (no drying), and the resulting solid was triturated with CH₂Cl₂. The filtrated was concentrated in vacuo, then purification by ISCO CombiFlash (100:0 to 80:20 hexanes:EtOAc) provided additional solid, which was combined with the triturated material to provide the title compound. ¹HNMR (400 MHz, CDCl₃): δ 8.27 (d, J=5.3 Hz, 1 H); 7.74 (d, J=5.3 Hz, 1 H); 7.50 (s, 1 H); 7.09 (s, 1 H); 6.81 (t, J=2.0 Hz, 1 H).

Step 4(d): 4-bromo-3-(3-chloro-5-iodophenoxy)pyridin-2-ol (4-5)

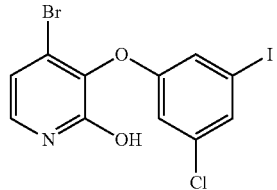 [SMILES: Oc1nccc(Br)c1Oc1cc(Cl)cc(I)c1]

To a solution of the dibromide (2.75 g; 5.62 mmol) in t-BuOH (23 mL) was added KOH (0.946 g; 16.9 mmol), and the mixture was heated to 75° C. overnight, which showed a 4:1 mixture of the desired product and its 2-bromo-4-hydroxy isomer. The mixture was diluted with aqueous saturated NaHCO₃, and extracted three times with EtOAc. The combined organic extracts were dried (MgSO₄) and concentrated in vacuo. The resulting solid was triturated with MeOH to provide the title compound as a white solid. $^1$H NMR (400 MHz, MeOD): δ 7.48 (t, J=1.5 Hz, 1 H); 7.33 (d, J=7.1 Hz, 1 H); 7.20 (t, J=1.7 Hz, 1 H); 6.94 (t, J=2.0 Hz, 1 H); 6.70 (d, J=7.1 Hz, 1 H).

Step 4(e): 3-[(4-bromo-2-hydroxypyridin-3-yl)oxy]-5-chlorobenzonitrile (4-6)

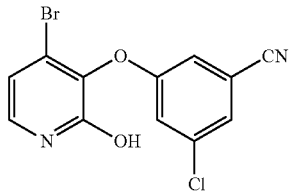 [SMILES: N#Cc1cc(Cl)cc(Oc2c(Br)ccnc2O)c1]

A solution of 4-bromo-3-(3-chloro-5-iodophenoxy)pyridin-2-ol (4-5; 1.72 g; 4.03 mmol) in DMF was purged with $N_2$ for 5 minutes. Zinc(II)cyanide (0.284 g; 2.42 mmol) and Pd(PPh$_3$)$_4$ (0.466 g; 0.403 mmol) were added, and the mixture was heated to 40° C. overnight. After cooling to room temperature, the mixture was diluted with aqueous saturated NaHCO$_3$ and extracted three times with CH$_2$Cl$_2$. The combined organic extracts were dried (MgSO$_4$) and concentrated in vacuo. Trituration of the resulting solid with water, then MeOH, then Et$_2$O provided the title compound as a white solid. $^1$H NMR (400 MHz, DMSO): δ 12.33 (s, 1 H); 7.73 (s, 1 H); 7.51 (s, 1 H); 7.44 (s, 1 H); 7.36 (d, J=7.1 Hz, 1 H); 6.56 (d, J=7.0 Hz, 1 H).

Steps 4(f) and (g): 3-({4-bromo-1-[(4-methyl-5-oxo-4,5-dihydro-1H-1,2,4-triazol-3-yl)methyl]-2-oxo-1,2-dihydropyridin-3-yl}oxy)-5-chlorobenzonitrile (4-1)

The title compound was prepared using modifications of Steps 1(e) and (f), replacing 3-chloro-5-{[2-hydroxy-4-(trifluoromethyl)pyridin-3-yl]oxy}benzonitrile (1-4) in Step 1(e) with 3-[(4-bromo-2-hydroxypyridin-3-yl)oxy]-5-chlorobenzonitrile (4-6). $^1$H NMR (400 MHz, DMSO): δ 11.66 (s, 1 H); 7.74 (s, 1 H); 7.65 (d, J=7.5 Hz, 1 H); 7.53 (s, 1 H); 7.43 (s, 1H); 6.73 (d, J=7.4 Hz, 1 H); 5.10 (s, 2 H); 3.11 (s, 3 H).

EXAMPLE 5

3-Chloro-5-({4-(1,1-difluoroethyl)-1-[(4-methyl-5-oxo-4,5-dihydro-1H-1,2,4-triazol-3-yl)methyl]-2-oxo-1,2-dihydropyridin-3-yl}oxy)benzonitrile (5-1)

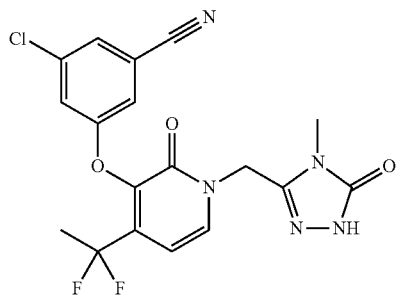 [SMILES: Cn1c(Cn2ccc(C(C)(F)F)c(Oc3cc(Cl)cc(C#N)c3)c2=O)n[nH]c1=O]

Step 5(a): 3-chloro-5-{[4-(1-ethoxyethenyl)-2-hydroxypyridin-3-yl]oxy}benzonitrile (5-2)

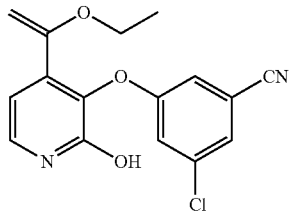 [SMILES: C=C(OCC)c1ccnc(O)c1Oc1cc(Cl)cc(C#N)c1]

A solution of 3-[(4-bromo-2-hydroxypyridin-3-yl)oxy]-5-chlorobenzonitrile (4-6; 300 mg; 0.922 mmol) and tributyl(1-ethoxyvinyl)tin (832 mg; 2.30 mmol) in DMF (4 mL) was degassed with $N_2$ for 5 minutes. Pd(PPh$_3$)$_4$ (53 mg; 0.046 mmol) was added, and the mixture was heated to 80° C. overnight. After cooling to room temperature, aqueous KF (2.3 M, 5 mL) was added, and the resulting precipitate was removed by filtration and washed with EtOAc. After phase separation, the aqueous phase was further extracted with EtOAc, then the combined organic extracts were dried (MgSO$_4$) and concentrated in vacuo. Purification by ISCO CombiFlash (100:0 to 0:100 hexanes:EtOAc) provided the title compound contaminated with residual triphenylphosphine oxide, which was carried forward without further purification. $^1$HNMR (400 MHz, MeOD): δ 7.45 (s, 1 H); 7.40 (d, J=6.9 Hz, 1 H); 7.19 (s, 1 H); 7.17 (s, 1 H); 6.58 (d, J=5.8 Hz, 1 H); 4.66 (d, J=2.9 Hz, 1 H); 4.52 (d, J=2.9 Hz, 1 H); 3.78 (dd, J=14.0, 7.0 Hz, 2 H); 1.17-1.09 (m, 3 H).

Step 5(b): 3-[(4-acetyl-2-hydroxypyridin-3-yl)oxy]-5-chlorobenzonitrile (5-3)

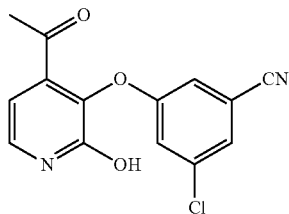 [SMILES: CC(=O)c1ccnc(O)c1Oc1cc(Cl)cc(C#N)c1]

To a solution of 3-chloro-5-{[4-(1-ethoxyethenyl)-2-hydroxypyridin-3-yl]oxy}benzonitrile (5-2; 157 mg; contains O=PPh$_3$) in acetone (2.5 mL) was added 1.0 mL of aqueous 10% HCl, and the mixture was stirred for 2 days. Acetone was removed in vacuo, then the mixture was diluted with water and extracted three times with CH$_2$Cl$_2$. The combined organic extracts were dried (MgSO$_4$) and concentrated in vacuo. Trituration with Et$_2$O provided the title compound as a white solid. $^1$H NMR (400 MHz, MeOD): δ7.53 (s, 1 H); 7.45 (d, J=6.9 Hz, 1 H); 7.34 (s, 1 H); 7.31 (s, 1 H); 6.58 (d, J=6.9 Hz, 1 H); 2.51 (s, 3 H).

Step 5(c): 3-chloro-5-{[4-(1,1-difluoroethyl)-2-hydroxypyridin-3-yl]oxy}benzonitrile (5-4)

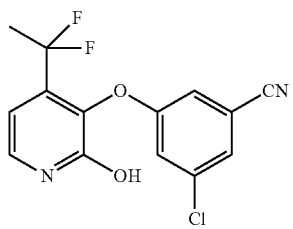 [SMILES: CC(F)(F)c1ccnc(O)c1Oc1cc(Cl)cc(C#N)c1]

To a solution of 3-[(4-acetyl-2-hydroxypyridin-3-yl)oxy]-5-chlorobenzonitrile (5-3; 102 mg; 0.353 mmol) in CH$_2$Cl$_2$ (1.4 mL) was added DAST (233 μL; 1.77 mmol) and the mixture was stirred at room temperature. Additional equivalents of DAST were added at 4 hours, 24 hours and 32 hours, and stirring continued for 48 hours, at which point LCMS analysis showed complete conversion. The reaction was quenched by the careful addition of aqueous saturated NaHCO$_3$, and then the product was extracted three times with CH$_2$Cl$_2$. The combined organic extracts were dried (MgSO$_4$) and concentrated in vacuo, to provide the title compound which was used directly without further purification.

Steps 5(d) and (e): 3-chloro-5-({4-(1,1-difluoroethyl)-1-[(4-methyl-5-oxo-4,5-dihydro-1H-1,2,4-triazol-3-yl)methyl]-2-oxo-1,2-dihydropyridin-3-yl}oxy)benzonitrile (5-1)

The title compound was prepared using modifications of Steps 1(e) and (f), replacing 3-chloro-5-{[2-hydroxy-4-(trifluoromethyl)pyridin-3-yl]oxy}benzonitrile (1-4) in Step 1(e) with 3-chloro-5-{[4-(1,1-difluoroethyl)-2-hydroxypyridin-3-yl]oxy}benzonitrile (5-4). $^1$HNMR (400 MHz, DMSO): δ 11.68 (s, 1 H); 7.80 (d, J=7.3 Hz, 1 H); 7.72 (t, J=1.5 Hz, 1H); 7.51 (dd, J=2.4, 1.3 Hz, 1 H); 7.41 (t, J=2.1 Hz, 1 H); 6.51 (d, J=7.3 Hz, 1 H); 5.15 (s, 2 H); 3.12 (s, 3 H); 1.95 (t, J=19.4 Hz, 3 H).

EXAMPLE 6

3-({5-Bromo-4-chloro-1-[(4-methyl-5-oxo-4,5-dihydro-1H-1,2,4-triazol-3-yl)methyl]-2-oxo-1,2-dihydropyridin-3-yl}oxy)-5-chlorobenzonitrile (6-1)

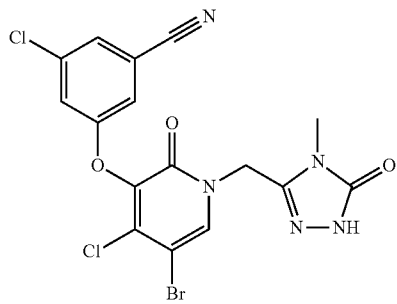 [SMILES: Cn1c(Cn2cc(Br)c(Cl)c(Oc3cc(Cl)cc(C#N)c3)c2=O)n[nH]c1=O]

Step 6(a): 3-[(5-bromo-4-chloro-2-hydroxypyridin-3-yl)oxy]-5-chlorobenzonitrile (6-2)

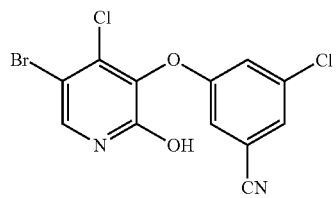 [SMILES: N#Cc1cc(Cl)cc(Oc2c(O)ncc(Br)c2Cl)c1]

To a suspension of 3-[(4-bromo-2-hydroxypyridin-3-yl)oxy]-5-chlorobenzonitrile (4-6; 1.5 g, 5.34 mmol) in acetonitrile (30 mL) was added NBS (1.5 g, 8.43 mmol). The mixture was stirred at room temperature for 2-3 hours, until LCMS analysi showed complete conversion. Water (20 mL) was added, and the solid was collected, washed successively with water, MeOH and Et$_2$O to give the bromide as a pale yellow solid of sufficient purity to be used directly. $^1$HNMR (400 MHz, DMSO): δ 12.67 (s, 1 H); 7.92 (s, 1 H); 7.74 (s, 1 H); 7.61 (s, 1 H); 7.57 (s, 1 H).

Steps 6(b) and (c)3: 3-({5-bromo-4-chloro-1-[(4-methyl-5-oxo-4,5-dihydro-1H-1,2,4-triazol-3-yl)methyl]-2-oxo-1,2-dihydropyridin-3-yl}oxy)-5-chlorobenzonitrile (6-1)

The title compound was prepared using modifications of Steps 1(e) and (f), replacing 3-chloro-5-{[2-hydroxy-4-(trifluoromethyl)pyridin-3-yl]oxy}benzonitrile (1-4) in Step 1(e) with 3-[(5-bromo-4-chloro-2-hydroxypyridin-3-yl)oxy]-5-chlorobenzonitrile (6-2). $^1$HNMR (400 MHz, DMSO): δ 11.70 (s, 1 H); 8.26 (s, 1 H); 7.76 (s, 1 H); 7.64 (s, 1 H); 7.57 (t, J=2.0 Hz, 1 H); 5.12 (s, 2 H); 3.13 (s, 3 H).

EXAMPLE 7

3-({5-Bromo-1-[(4-methyl-5-oxo-4,5-dihydro-1H-1,2,4-triazol-3-yl)methyl]-2-oxo-4-(trifluoromethyl)-1,2-dihydropyridin-3-yl}oxy)-5-chlorobenzonitrile (7-1)

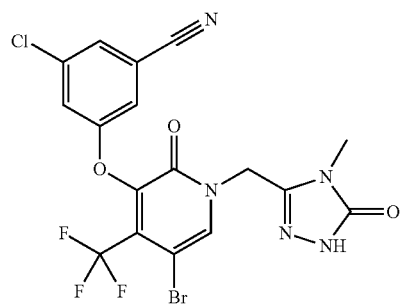 [SMILES: Cn1c(Cn2cc(Br)c(C(F)(F)F)c(Oc3cc(Cl)cc(C#N)c3)c2=O)n[nH]c1=O]

Step 7(a): 3-{[5-bromo-2-hydroxy-4-(trifluoromethyl)pyridin-3-yl]oxy}-5-chlorobenzonitrile (7-2)

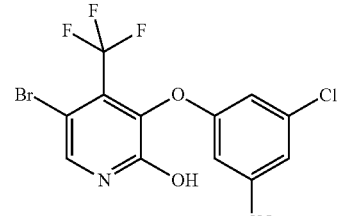

To a suspension of 3-[(4-bromo-2-hydroxypyridin-3-yl)oxy]-5-chlorobenzonitrile (4-6; 1.30 g, 4.13 mmol) in acetonitrile (30 mL) was added NBS (0.800 g, 4.49 mmol). The mixture was stirred at room temperature for 2-3 hours, until LCMS analysi showed complete conversion. Water (20 mL) was added, and the solid was collected, washed successively with water, MeOH and Et$_2$O to give the bromide as a pale yellow solid of sufficient purity to be used directly. $^1$HNMR (400 MHz, DMSO): δ 12.94 (s, 1 H); 7.95 (s, 1 H); 7.74 (s, 1 H); 7.67 (s, 1H); 7.63 (s, 1 H).

Steps 7(b) and (c): 3-({5-bromo-1-[(4-methyl-5-oxo-4,5-dihydro-1H-1,2,4-triazol-3-yl)methyl]-2-oxo-4-(trifluoromethyl)-1,2-dihydropyridin-3-yl}oxy)-5-chlorobenzonitrile (7-1)

The title compound was prepared using modifications of Steps 1(e) and (f), replacing 3-chloro-5-{[2-hydroxy-4-(trifluoromethyl)pyridin-3-yl]oxy}benzonitrile (1-4) in Step 1(e) with 3-{[5-bromo-2-hydroxy-4-(trifluoromethyl)pyridin-3- yl]oxy}-5-chlorobenzonitrile (7-2). $^1$H NMR (400 MHz, DMSO): δ 11.73 (s, 1 H); 8.25 (s, 1 H); 7.76 (d, J=1.7 Hz, 1 H); 7.71-7.69 (m, 1 H); 7.66-7.64 (m, 1 H); 5.14 (s, 2 H); 3.11 (s, 3 H).

EXAMPLE 8

3-(Difluoromethyl)-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile (8-1)

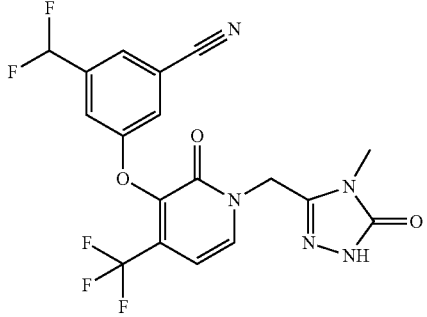 [SMILES: Cn1c(Cn2ccc(C(F)(F)F)c(Oc3cc(C#N)cc(C(F)F)c3)c2=O)n[nH]c1=O]

Step 8(a): 5-[(benzyloxy)methyl]-4-methyl-2,4-dihydro-3H-1,2,4-triazol-3-one (8-2)

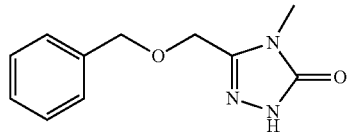 [SMILES: Cn1c(COCc2ccccc2)n[nH]c1=O]

To a solution of N-methylhydrazinecarboxamide (3.13 g; 35.1 mmol; Can. J. Chem. 1951, 29, 478) in THF was added benzyloxyacetyl chloride (5.45 mL; 35.1 mmol). The mixture was cooled to 0° C., then 5 M NaOH(aq) (7.38 mL; 36.9 mmol) was added and the mixture was stirred for 2 hours. After concentration in vacuo, the unpurified 2-[(benzyloxy)acetyl]-N-methylhydrazinecarboxamide was dissolved in 2 M NaOH(aq) (60 mL), and the mixture was heated to 95° C. overnight. After cooling to room temperature, the mixture was neutralized by the dropwise addition of aqueous 6 M HCl. After dilution with water, the aqueous layer was extracted twice with EtOAc. The combined organic extracts were dried (Na$_2$SO$_4$) and concentrated in vacuo. Purification by ISCO CombiFlash (80:20 to 0:100 hexanes:EtOAc) provided the title compound. $^1$H NMR (500 MHz, CDCl$_3$): δ 10.03 (s, 1 H); 7.43-7.34 (m, 5 H); 4.57 (s, 2 H); 4.47 (s, 2 H); 3.35 (s, 3 H).

Step 8(b): 5-(hydroxymethyl)-4-methyl-2,4-dihydro-3H-1,2,4-triazol-3-one (8-3)

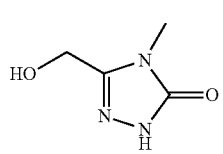

To a suspension of 5-[(benzyloxy)methyl]-4-methyl-2,4-dihydro-3H-1,2,4-triazol-3-one (8-2; 4.20 g; 19.2 mmol) in EtOH (84 mL) was added Pd(OH)$_2$ (20 wt %; 2.02 g; 2.87 mmol) and the mixture was stirred overnight at room temperature. Filtration through Solka Floc, and in vacuo concentration provided 2.33 g (18.1 mmol; 94%) of the title compound of sufficient purity to be used directly. $^1$H NMR (500 MHz, DMSO): δ 11.53 (s, 1 H); 5.51 (t, J=5.7 Hz, 1 H); 4.33 (d, J=5.8 Hz, 2 H); 3.17 (s, 3 H).

Step 8(c): 5-(chloromethyl)-4-methyl-2,4-dihydro-3H-1,2,4-triazol-3-one (8-4)

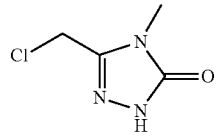

To a suspension of 5-(hydroxymethyl)-4-methyl-2,4-dihydro-3H-1,2,4-triazol-3-one (8-3; 2.33 g; 18.0 mmol) in CH$_3$CN (47 mL) was added thionyl chloride (1.52 mL; 20.7 mmol) and the mixture was stirred at room temperature for 5 hours. After in vacuo concentration, the resulting residue was triturated with hexanes to provide the title compound as a white solid. $^1$H NMR (500 MHz, DMSO): δ 11.87 (s, 1 H); 4.75 (s, 2 H); 3.21 (s, 3 H).

Step 8(d): 3-fluoro-4-(trifluoromethyl)pyridin-2-ol (8-5)

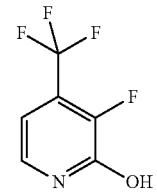

A solution of 3-fluoro-4-(trifluoromethyl)pyridine (5.00 g; 30.3 mmol) in CH$_2$Cl$_2$ (10 mL) was cooled to 0° C., then methyltrioxorhenium(VII) (0.062 g; 0.249 mmol) and hydrogen peroxide (30%; 6.2 mL; 61 mmol) were added and the mixture was warmed to room temperature. After stirring for 2 hours, the reaction was quenched by the addition of MnO$_2$ (5 mg) and 30 minutes additional stirring. After dilution with additional CH$_2$Cl$_2$, the mixture was filtered through Solka Floc, dried (MgSO$_4$) and concentrated in vacuo to provide 3-fluoro-4-(trifluoromethyl)pyridine 1-oxide of sufficient purity to be used directly. The N-oxide (3.70 g; 20.4 mmol) was dissolved in trifluoroacetic anhydride (21.6 mL; 153 mmol) in a hydrogenation bomb and heated to 85° C. for 15 hours. After cooling to 0° C., water was added, followed by solid K$_2$CO$_3$ until pH 9. The aqueous fraction was extracted with EtOAc and Me-THF, and the combined organic extracts were dried (MgSO$_4$) and concentrated in vacuo. Purification by ISCO CombiFlash (70:30 to 0:100 hexanes:EtOAc) provided the title compound as a pink solid. $^1$H NMR (400 MHz, Acetone): δ 11.48 (s, 1 H); 7.55 (d, J=7.1 Hz, 1 H); 6.39 (t, J=6.2 Hz, 1 H).

Step 8(e): 3-(difluoromethyl)benzonitrile (8-6)

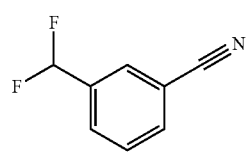 [SMILES: N#Cc1cccc(C(F)F)c1]

To a solution of 3-cyanobenzaldehyde (1.00 g; 7.63 mmol) in CH$_2$Cl$_2$ (38 mL) was added DAST (1.01 mL; 7.63 mmol) and the mixture was stirred for 1 hour at room temperature. The reaction was quenched with aqueous 1 N HCl and extracted twice with CH$_2$Cl$_2$. The combined organic extracts were dried and concentrated in vacuo. Purification by ISCO CombiFlash provided the title compound as a yellow oil. $^1$H NMR (400 MHz, DMSO): δ 8.09 (s, 1 H); 8.05 (d, J=7.8 Hz, 1 H); 7.94 (d, J=7.9 Hz, 1 H); 7.80-7.71 (m, 1 H); 7.12 (t, J=55.4 Hz, 1 H).

Step 8(e): 3-(difluoromethyl)-5-hydroxybenzonitrile (8-7)

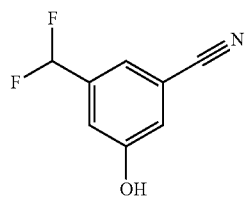 [SMILES: N#Cc1cc(O)cc(C(F)F)c1]

The title compound was prepared using a modification of step 4(a), replacing 1-chloro-3-iodobenzene with 3-(difluoromethyl)benzonitrile (8-6), and hexanes as solvent with MTBE. $^1$HNMR (400 MHz, DMSO): δ 10.69 (s, 1 H); 7.46 (s, 1 H); 7.32 (s, 1 H); 7.26 (s, 1 H); 7.02 (t, J=55.4 Hz, 1 H).

Step 8(f): 3-fluoro-1-[(4-methyl-5-oxo-4,5-dihydro-1H-1,2,4-triazol-3-yl)methyl]-4-(trifluoromethyl)pyridin-2(1H)-one (8-8)

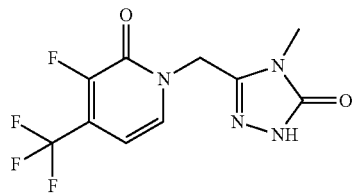 [SMILES: Cn1c(Cn2ccc(C(F)(F)F)c(F)c2=O)n[nH]c1=O]

To a solution of 3-fluoro-4-(trifluoromethyl)pyridin-2-ol (8-5; 50 mg; 0.34 mmol) in dioxane 1.7 mL) was added K$_2$CO$_3$ (51 mg; 0.373 mmol) and the mixture was stirred for 5minutes. 5-(chloromethyl)-4-methyl-2,4-dihydro-3H-1,2,4-triazol-3-one (8-4; 68 mg; 0.373 mmol) was then added, and the mixture was stirred for 2 hours at room temperature. The mixture was diluted with water, and extracted with CH$_2$Cl$_2$. The organic extracts were dried (MgSO$_4$) and concentrated in vacuo. Purification by ISCO CombiFlash provided the title compound. $^1$H NMR (400 MHz, CDCl$_3$): δ 10.14 (s, 1 H); 8.11 (d, J=5.2 Hz, 1 H); 7.18 (t, J=4.7 Hz, 1 H); 5.40 (s, 2 H); 3.41 (s, 3 H).

Step 8(g): 3-(difluoromethyl)-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile (8-1)

A mixture of 3-fluoro-1-[(4-methyl-5-oxo-4,5-dihydro-1H-1,2,4-triazol-3-yl)methyl]-4-(trifluoromethyl)pyridin-2 (1 H)-one (8-8; 30 mg; 0.103 mmol), 3-(difluoromethyl)-5-hydroxybenzonitrile (8-7; 34.7 mg; 0.205 mmol) and K$_2$CO$_3$ (28.4 mg; 0.205 mmol) was heated to 75° C., and stirred overnight. After cooling to room temperature, the mixture was diluted with water and extracted with CH$_2$Cl$_2$. The combined organic extracts were dried (MgSO$_4$) and concentrated in vacuo. Purification by mass-directed HPLC provided 2.1 mg (0.0048 mmol; 4.6%) of the title compound as a white solid. $^1$H NMR (400 MHz, DMSO): δ 11.70 (s, 1 H); 7.90 (d, J=7.3 Hz, 1 H); 7.80 (d, J=8.5 Hz, 2 H); 7.57 (s, 1 H); 7.05 (t, J=55.2 Hz, 1 H); 6.69 (d, J=7.3 Hz, 1 H); 5.17 (s, 2 H); 3.10 (s, 3 H).

EXAMPLE 9

ECL Assay for Inhibition of HIV Reverse Transcriptase

An assay to determine the in vitro inhibition of HIV reverse transcriptase by compounds of the present invention was conducted as follows: HIV-1 RT enzyme (0.1 nM) was combined with inhibitor or DMSO (10%) in assay buffer (50 mM Tris-HCl, pH 7.8, 1 mM dithiothreitol, 6 mM MgCl$_2$, 80 mM KCl, 0.025% CHAPS, 0.1 mM EGTA), and the mixture pre-incubated for 30 minutes at room temperature in microtiter plates (Corning Costar #3365). 50 μL reaction mixtures were initiated with a combination of primer-template substrate (5 nM final concentration) and dNTPs (0.6 μM dNTPs, 20 nM Ruthenium-dUTP). The heterodimeric nucleic acid substrate was generated by annealing the DNA primer biotinylated-pD500 (obtained from Integrated DNA Technologies) to t500, a 500 nucleotide RNA template created by in vitro transcription (see Shaw-Reid et al., *J. Biol. Chem.*, 278: 2777-2780). After a 90 minute incubation at 37° C., reactions were quenched by 60 μL of quenching buffer containing 0.05 M EDTA, 0.7% BSA, 0.07% Tween-20 and 0.017% sodium azide in PBS. After a 10 minute incubation, 50 μL of the quenched reaction was transfered to a MesoScale Discovery (MSD) Avidin standard plate, previously blocked for 1 hour with 5% blocker A (from MSD). The plate is then left at room temperature for 1 hour, after which it is washed 3 times with 200 μL per well of PBS. 150 μL of 1× read buffer T (MSD) is added and the plate read on the Sector Imager 6000 (MSD). Representative compounds of the present invention exhibit inhibition of the reverse transcriptase enzyme in this assay. For example, the title compounds set forth above in Examples 1-8 were tested in the assay and were found to have percent inhibition values at 100 nM as set forth in Table B below.

TABLE B

| Example No. | ECL Assay (WT) % Inhibition at 100 nM |
|---|---|
| 1-1 | 85 |
| 2-1 | 75 |
| 3-1 | 75 |
| 4-1 | 90 |
| 5-1 | 75 |
| 6-1 | 90 |
| 7-1 | 77 |
| 8-1 | 75 |

WT = wild-type

EXAMPLE 10

Assay for Inhibition of HIV Replication

Assays for the inhibition of acute HIV-1 infection of T-lymphoid cells (alternatively referred to herein as the "spread assay") were conducted in accordance with Vacca, J. P. et al., *Proc. Natl. Acad. Sci. USA* 1994, 91: 4096. Representative compounds of the present invention exhibit inhibition of HIV replication in the assay employing wild-type HIV-1. For example, the compounds set forth in Examples 1 to 8 were found to have CIC$_{95}$ values as set forth in Table C. The compounds were also tested using a variant of the assay using HIV strains containing the K103N and Y181C mutants, and found to be less than 20-fold shifted relative to wild-type in all cases.

TABLE C

| Example No. | Spread (WT) CIC$_{95}$ (nM) (50% NHS) | Spread (WT) CIC$_{95}$ (nM) (10% FBS) |
|---|---|---|
| 1-1 | 19 | — |
| 2-1 | 26 | — |
| 3-1 | 15 | — |
| 4-1 | 12 | — |
| 5-1 | 10 | — |
| 6-1 | — | 5.1 |
| 7-1 | 23 | — |
| 8-1 | — | 7.3 |

WT = wild type

EXAMPLE 11

Cytotoxicity

Cytotoxicity was determined by microscopic examination of the cells in each well in the spread assay, wherein a trained analyst observed each culture for any of the following morphological changes as compared to control cultures: pH imbalance, cell abnormality, cytostatic, cytopathic or crystallization (i.e. the compound is not soluble or forms crystals in the well). Representative compounds of the present invention exhibited no cytotoxicity up to the top dose studied in these assays at concentrations at or above their CIC95 value in the spread assay. For example, the title compounds of Examples 1 to 8 exhibited no cytotoxicity up to 125 nM.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entireties into the disclosure.

What is claimed is:

1. The compound

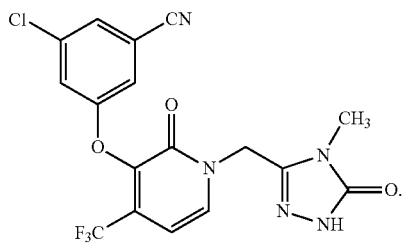 [SMILES: Cn1c(Cn2ccc(C(F)(F)F)c(Oc3cc(Cl)cc(C#N)c3)c2=O)n[nH]c1=O]

2. A pharmaceutical composition comprising an effective amount of the compound according to claim 1 and a pharmaceutically acceptable carrier.

3. A method for the treatment of infection by HIV or for the treatment of AIDS in a subject in need thereof which comprises administering to the subject an effective amount of the compound according to claim 1.

4. The compound

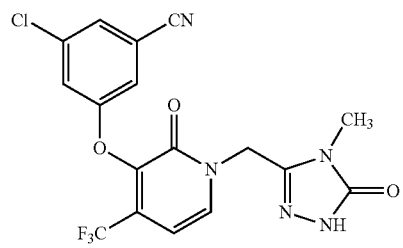 [SMILES: Cn1c(Cn2ccc(C(F)(F)F)c(Oc3cc(Cl)cc(C#N)c3)c2=O)n[nH]c1=O]

or a pharmaceutically acceptable salt thereof.

5. A pharmaceutical composition comprising an effective amount of the compound according to claim 4 and a pharmaceutically acceptable carrier.

6. A method for the treatment of infection by HIV or for the treatment of AIDS in a subject in need thereof which comprises administering to the subject an effective amount of the compound according to claim 4.

* * * * *